United States Patent
Sehl et al.

(10) Patent No.: US 8,617,584 B2
(45) Date of Patent: Dec. 31, 2013

(54) ADHESIVE TISSUE REPAIR PATCH AND COLLAGEN SHEETS

(75) Inventors: Louis C. Sehl, Redwood City, CA (US); Olof Mikael Trollsas, Los Gatos, CA (US); Donald G. Wallace, Menlo Park, CA (US); David Toman, Atherton, CA (US); Frank A. DeLustro, Belmont, CA (US); Jacqueline A. Schroeder, Boulder Creek, CA (US); George H. Chu, Cupertino, CA (US)

(73) Assignee: Angiodevice International GmbH, Zug (CH)

( * ) Notice: Subject to any disclaimer, the term of this patent is extended or adjusted under 35 U.S.C. 154(b) by 415 days.

(21) Appl. No.: 12/787,304

(22) Filed: May 25, 2010

(65) Prior Publication Data

US 2010/0233246 A1 Sep. 16, 2010

Related U.S. Application Data

(60) Continuation of application No. 10/971,684, filed on Oct. 22, 2004, now Pat. No. 8,377,466, which is a division of application No. 10/262,640, filed on Sep. 30, 2002, now Pat. No. 6,833,408, which is a continuation-in-part of application No. 09/883,138, filed on Jun. 15, 2001, now Pat. No. 6,458,889, which is a continuation-in-part of application No. 09/649,337, filed on Aug. 28, 2000, now Pat. No. 6,495,127.

(60) Provisional application No. 60/151,273, filed on Aug. 27, 1999.

(51) Int. Cl.
*A61F 13/00* (2006.01)

(52) U.S. Cl.
USPC .......................................................... 424/422

(58) Field of Classification Search
None
See application file for complete search history.

(56) References Cited

U.S. PATENT DOCUMENTS

| | | |
|---|---|---|
| 3,619,371 A | 11/1971 | Crook et al. |
| 3,742,955 A | 7/1973 | Battista et al. |
| 3,788,948 A | 1/1974 | Kegadal et al. |
| 3,810,473 A | 5/1974 | Cruz, Jr. et al. |
| 3,876,501 A | 4/1975 | Hanushewsky |

(Continued)

FOREIGN PATENT DOCUMENTS

| | | |
|---|---|---|
| CA | 2134744 A1 | 5/1995 |
| EP | 0013249 B1 | 7/1980 |

(Continued)

OTHER PUBLICATIONS

Abuchowski et al. (1977), "Alteration of immunological properties of bovine serum albumin by covalent attachment of polyethylene glycol," *Biol. Chem.* 252(11):3578-3581.

(Continued)

*Primary Examiner* — Paul Dickinson
(74) *Attorney, Agent, or Firm* — Seed IP Law Group PLLC

(57) ABSTRACT

The present invention relates generally to synthetic polymer compositions that form interpenetrating polymer networks. In a preferred embodiment, the compositions comprise two multifunctionally activated synthetic polymers, along with a tensile strength enhancer. Such compositions form matrices that exhibit superior cohesive strength and in many instances can serve as adequate replacements for surgical means of attaching tissues, such as sutures, sponges and medical staples.

5 Claims, 13 Drawing Sheets

(56) References Cited

U.S. PATENT DOCUMENTS

| | | |
|---|---|---|
| 3,949,073 A | 4/1976 | Daniels et al. |
| 3,960,830 A | 6/1976 | Bayer et al. |
| 4,002,531 A | 1/1977 | Royer |
| 4,008,341 A | 2/1977 | Kehr ............................ 427/44 |
| 4,055,635 A | 10/1977 | Green et al. |
| 4,088,538 A | 5/1978 | Schneider |
| 4,101,380 A | 7/1978 | Rubinstein et al. |
| 4,164,559 A | 8/1979 | Miyata et al. |
| 4,175,073 A | 11/1979 | Carlsson et al. .......... 260/112 R |
| 4,179,337 A | 12/1979 | Davis et al. |
| 4,192,021 A | 3/1980 | Deibig et al. |
| 4,237,229 A | 12/1980 | Hartdegen et al. ............ 435/182 |
| 4,238,480 A | 12/1980 | Sawyer |
| 4,261,973 A | 4/1981 | Lee et al. |
| 4,279,812 A | 7/1981 | Cioca |
| 4,301,144 A | 11/1981 | Iwashita et al. |
| 4,314,380 A | 2/1982 | Miyata |
| 4,320,201 A | 3/1982 | Berg et al. |
| 4,357,274 A | 11/1982 | Werner |
| 4,390,519 A | 6/1983 | Sawyer |
| 4,404,970 A | 9/1983 | Sawyer |
| 4,412,947 A | 11/1983 | Cioca |
| 4,412,989 A | 11/1983 | Iwashita |
| 4,414,147 A | 11/1983 | Klibanov et al. |
| 4,415,628 A | 11/1983 | Cioca |
| 4,415,665 A | 11/1983 | Mosbach et al. |
| 4,424,208 A | 1/1984 | Wallace et al. |
| 4,451,568 A | 5/1984 | Sneider et al. |
| 4,461,298 A | 7/1984 | Shalaby et al. ............ 128/335.5 |
| 4,488,911 A | 12/1984 | Luck et al. |
| 4,495,285 A | 1/1985 | Shimizu et al. |
| 4,496,689 A | 1/1985 | Mitra |
| 4,515,637 A | 5/1985 | Cioca |
| 4,544,516 A | 10/1985 | Hughes et al. |
| 4,553,974 A | 11/1985 | Dewanjee |
| 4,557,764 A | 12/1985 | Chu, II |
| 4,563,350 A | 1/1986 | Nathan et al. |
| 4,563,351 A | 1/1986 | Caslavsky et al. |
| 4,563,490 A | 1/1986 | Stol et al. |
| 4,578,067 A | 3/1986 | Cruz, Jr. |
| 4,582,640 A | 4/1986 | Smestad et al. |
| 4,584,188 A | 4/1986 | Graham ........................ 424/19 |
| 4,592,864 A | 6/1986 | Miyata et al. |
| 4,600,533 A | 7/1986 | Chu |
| 4,642,117 A | 2/1987 | Nguyen |
| 4,655,980 A | 4/1987 | Chu |
| 4,670,417 A | 6/1987 | Iwasaki et al. |
| 4,678,468 A | 7/1987 | Hiroyoshi |
| 4,687,820 A | 8/1987 | Hou et al. |
| 4,689,399 A | 8/1987 | Chu |
| 4,695,602 A | 9/1987 | Crosby et al. |
| 4,703,108 A | 10/1987 | Silver et al. |
| 4,704,131 A | 11/1987 | Noishiki et al. |
| 4,725,671 A | 2/1988 | Chu et al. |
| 4,732,863 A | 3/1988 | Tomasi |
| 4,737,544 A | 4/1988 | McCain |
| 4,745,180 A | 5/1988 | Moreland et al. |
| 4,766,106 A | 8/1988 | Katre |
| 4,774,227 A | 9/1988 | Piez |
| 4,789,663 A | 12/1988 | Wallace et al. |
| 4,795,467 A | 1/1989 | Piez et al. |
| 4,828,563 A | 5/1989 | Müller-Lierheim |
| 4,829,099 A | 5/1989 | Fuller et al. ................... 523/111 |
| 4,839,345 A | 6/1989 | Doi et al. ........................ 514/21 |
| 4,847,325 A | 7/1989 | Shadle et al. |
| 4,851,513 A | 7/1989 | Devore et al. |
| 4,859,533 A * | 8/1989 | Seiya et al. ................... 428/366 |
| 4,886,866 A | 12/1989 | Braatz et al. .................... 528/59 |
| 4,935,465 A | 6/1990 | Garman |
| 4,937,270 A | 6/1990 | Hamilton et al. |
| 4,950,483 A | 8/1990 | Ksander |
| 4,950,699 A | 8/1990 | Holman |
| 4,973,493 A | 11/1990 | Guire |
| 4,979,959 A | 12/1990 | Guire |
| 4,980,403 A | 12/1990 | Bateman et al. |
| 4,983,580 A | 1/1991 | Gibson |
| 5,017,229 A | 5/1991 | Burns et al. |
| 5,024,742 A | 6/1991 | Nesburn et al. |
| 5,104,957 A | 4/1992 | Kelman et al. |
| 5,122,614 A | 6/1992 | Zalipsky |
| 5,135,755 A | 8/1992 | Czech et al. .................... 424/445 |
| 5,141,747 A | 8/1992 | Scholz |
| 5,147,374 A | 9/1992 | Fernandez .................... 606/151 |
| 5,156,613 A | 10/1992 | Sawyer |
| 5,156,622 A | 10/1992 | Thompson |
| 5,162,430 A | 11/1992 | Rhee et al. .................... 525/54.2 |
| 5,167,960 A | 12/1992 | Ito et al. |
| 5,169,754 A | 12/1992 | Siiman et al. |
| 5,176,692 A | 1/1993 | Wilk et al. .................... 606/151 |
| 5,192,316 A | 3/1993 | Ting |
| 5,198,493 A | 3/1993 | Holmberg et al. |
| 5,201,764 A | 4/1993 | Kelman et al. |
| 5,204,110 A | 4/1993 | Cartmell et al. ............... 424/443 |
| 5,209,776 A | 5/1993 | Bass et al. |
| 5,219,564 A | 6/1993 | Zalipsky et al. |
| 5,219,895 A | 6/1993 | Kelman et al. |
| 5,264,214 A | 11/1993 | Rhee et al. |
| 5,290,552 A | 3/1994 | Sierra et al. |
| 5,292,802 A | 3/1994 | Rhee et al. |
| 5,298,643 A | 3/1994 | Greenwald |
| 5,304,595 A | 4/1994 | Rhee et al. |
| 5,306,500 A | 4/1994 | Rhee et al. |
| 5,308,889 A | 5/1994 | Rhee et al. .................... 523/113 |
| 5,321,095 A | 6/1994 | Greenwald |
| 5,324,775 A | 6/1994 | Rhee et al. |
| 5,324,844 A | 6/1994 | Zalipsky |
| 5,328,955 A | 7/1994 | Rhee et al. |
| 5,336,501 A | 8/1994 | Czech et al. ................... 424/445 |
| 5,349,001 A | 9/1994 | Greenwald et al. |
| 5,354,336 A | 10/1994 | Kelman et al. |
| 5,364,622 A | 11/1994 | Franz et al. |
| 5,405,366 A | 4/1995 | Fox et al. ......................... 607/50 |
| 5,405,877 A | 4/1995 | Greenwald et al. |
| 5,410,016 A | 4/1995 | Hubbell et al. |
| 5,426,148 A | 6/1995 | Tucker ........................ 524/496 |
| 5,428,022 A | 6/1995 | Palefsky et al. .................. 514/21 |
| 5,455,027 A | 10/1995 | Zalipsky et al. |
| 5,464,929 A | 11/1995 | Bezwada et al. ............. 528/361 |
| 5,475,052 A | 12/1995 | Rhee et al. |
| 5,496,872 A | 3/1996 | Constancis et al. |
| 5,505,952 A | 4/1996 | Jiang et al. .................... 424/423 |
| 5,510,418 A | 4/1996 | Rhee et al. .................... 525/54.2 |
| 5,514,379 A | 5/1996 | Weissleder et al. |
| 5,527,856 A | 6/1996 | Rhee et al. |
| 5,549,904 A | 8/1996 | Juergensen et al. |
| 5,550,172 A | 8/1996 | Regula et al. .................. 523/118 |
| 5,550,187 A | 8/1996 | Rhee et al. .................... 525/54.1 |
| 5,565,519 A | 10/1996 | Rhee et al. .................... 525/54.1 |
| 5,567,422 A | 10/1996 | Greenwald |
| 5,578,661 A | 11/1996 | Fox et al. ........................ 524/27 |
| 5,580,923 A | 12/1996 | Yeung et al. ................... 525/541 |
| 5,605,976 A | 2/1997 | Martinez et al. |
| 5,612,052 A | 3/1997 | Shalaby ........................ 424/426 |
| 5,612,460 A | 3/1997 | Zalipsky |
| 5,614,549 A | 3/1997 | Greenwald et al. |
| 5,614,587 A | 3/1997 | Rhee et al. |
| 5,626,863 A | 5/1997 | Hubbell et al. |
| 5,637,749 A | 6/1997 | Greenwald |
| 5,643,464 A | 7/1997 | Rhee et al. .................... 210/748 |
| 5,643,575 A | 7/1997 | Martinez et al. |
| 5,644,002 A | 7/1997 | Cooper et al. ................. 525/411 |
| 5,646,239 A | 7/1997 | Constancis et al. ........... 528/373 |
| 5,667,839 A | 9/1997 | Berg ............................ 426/657 |
| 5,681,904 A | 10/1997 | Manzara |
| 5,696,178 A | 12/1997 | Cooper et al. .................. 522/43 |
| 5,700,848 A | 12/1997 | Soon-Shiong et al. |
| 5,714,159 A | 2/1998 | Shalaby ........................ 424/426 |
| 5,733,563 A | 3/1998 | Fortier ........................ 424/422 |
| 5,736,589 A | 4/1998 | Cooper et al. .................. 522/43 |
| 5,752,974 A | 5/1998 | Rhee et al. .................... 606/214 |
| 5,760,200 A | 6/1998 | Miller et al. .................... 536/21 |
| 5,786,421 A | 7/1998 | Rhee et al. .................... 525/54.1 |
| 5,817,303 A | 10/1998 | Stedronsky et al. ........ 424/78.02 |
| 5,834,007 A | 11/1998 | Kubota ........................ 424/443 |

(56) References Cited

U.S. PATENT DOCUMENTS

| | | | |
|---|---|---|---|
| 5,874,500 | A | 2/1999 | Rhee et al. ............... 222/135 |
| 6,005,020 | A | 12/1999 | Loomis ................... 523/105 |
| 6,007,613 | A | 12/1999 | Izoret .................. 106/160.1 |
| 6,030,958 | A | 2/2000 | Burns et al. ............... 514/57 |
| 6,051,648 | A | 4/2000 | Rhee et al. .............. 525/54.1 |
| 6,149,931 | A | 11/2000 | Schwartz et al. ........... 424/427 |
| 6,166,130 | A | 12/2000 | Rhee et al. ................ 525/541 |
| 6,174,999 | B1 | 1/2001 | Miller et al. ............... 536/21 |
| 6,217,894 | B1 | 4/2001 | Sawhney et al. ........... 424/426 |
| 6,235,726 | B1 | 5/2001 | Burns et al. ............... 514/57 |
| 6,258,124 | B1 | 7/2001 | Darois et al. ............ 623/14.13 |
| 6,312,725 | B1 | 11/2001 | Wallace et al. ............ 424/484 |
| 6,323,278 | B2 | 11/2001 | Rhee et al. |
| 6,458,889 | B1 | 10/2002 | Trollsas et al. |
| 6,475,508 | B1 | 11/2002 | Schwartz et al. ........... 424/427 |
| 6,495,127 | B1 | 12/2002 | Wallace et al. ........... 424/78.03 |
| 6,559,119 | B1 | 5/2003 | Burgess et al. ............... 514/2 |
| RE38,158 | E | 6/2003 | Barrows et al. ............. 514/21 |
| 6,833,408 | B2 | 12/2004 | Sehl et al. ............... 525/54.1 |
| 2001/0055615 | A1 | 12/2001 | Wallace et al. ............ 424/484 |
| 2002/0042473 | A1 | 4/2002 | Trollsas et al. ........... 525/54.1 |
| 2002/0049503 | A1 | 4/2002 | Milbocker ............... 623/23.72 |
| 2004/0186231 | A1 | 9/2004 | Rhee et al. .............. 525/54.3 |

FOREIGN PATENT DOCUMENTS

| | | |
|---|---|---|
| EP | 0042253 | 12/1981 |
| EP | 0154447 | 9/1985 |
| EP | 0157359 | 10/1985 |
| EP | 0171176 | 2/1986 |
| EP | 0243179 | 10/1987 |
| EP | 0330389 | 8/1989 |
| EP | 0341007 | 11/1989 |
| EP | 0 424 143 A2 | 4/1991 |
| EP | 0431479 A1 | 6/1991 |
| EP | 0466383 | 1/1992 |
| EP | 0575273 | 12/1993 |
| EP | 0640647 | 3/1995 |
| EP | 0656214 A1 | 6/1995 |
| EP | 0656215 | 6/1995 |
| EP | 0680990 | 11/1995 |
| EP | 0732109 | 9/1996 |
| EP | 0747066 A2 | 12/1996 |
| FR | 2628634 | 7/1990 |
| GB | 697334 | 9/1953 |
| GB | 729122 | 5/1955 |
| GB | 1059455 | 2/1967 |
| JP | 61-204271 A | 9/1986 |
| JP | 2-70749 A | 3/1990 |
| JP | 4-7331 A | 1/1992 |
| JP | 4-227265 | 8/1992 |
| JP | 60-70972 | 3/1994 |
| JP | 07-090241 | 4/1995 |
| WO | WO 84/01106 | 3/1984 |
| WO | WO 85/04412 | 10/1985 |
| WO | WO 87/04078 | 7/1987 |
| WO | WO 90/05755 | 5/1990 |
| WO | WO 91/15368 A1 | 10/1991 |
| WO | WO 92/13025 | 8/1992 |
| WO | WO 92/13578 | 8/1992 |
| WO | WO 94/01483 | 1/1994 |
| WO | WO 94/03155 | 2/1994 |
| WO | 94/25503 A1 | 11/1994 |
| WO | WO 95/11924 A1 | 5/1995 |
| WO | 96/21469 A1 | 7/1996 |
| WO | WO 96/40780 A1 | 12/1996 |
| WO | WO 97/22371 | 6/1997 |
| WO | 97-28192 A1 | 8/1997 |
| WO | WO 99/07417 | 2/1999 |
| WO | WO 00/33764 | 6/2000 |
| WO | WO 00/44808 A1 | 8/2000 |
| WO | WO 00/62827 | 10/2000 |
| WO | WO 01/16210 A1 | 3/2001 |

OTHER PUBLICATIONS

Abuchowski et al. (1984), "Cancer therapy with chemically modified enzymes. I. Antitumor properties of polyethylene glycol-asparaginase conjugates," *Cancer Biochem. Biophys.* 7:175-186.

Abuchowski et al. (1977), "Effect of covalent attachment of polyethylene glycol on immunogenicity and circulating life of bovine liver catalase," *J. Biol. Chem.* 252(11):3582-3586.

Anderson et al., "The use of esters of n-hydroxysuccinimide in peptide synthesis," *J. Am. Chem Soc.* 86(9):1839-1842, 1964.

Beauchamp et al. (1983), "A new procedure for the synthesis of polyethylene glycol-protein adducts: Effects on function, receptor recognition, and clearance of superoxide dismutase, lactoferrin, and $a_2$-macroglobulin," *Analytical Biochemistry* 131:25-33.

Bendich et al. (1982), "Immunological effects of native and polyethylene glycol-modified asparaginases from *Vibro succinogenes* and *Escherichia coli* in normal and tumor-bearing mice," *Clin. Exp. Immunol.* 48:273-278.

Braatz et al. (1992), "A New Hydrophilic Polymer for Biomaterial Coatings with Low Protein Adsorption," *J. Biomater. Sci. Polymer Edn.* 3(6):451-462.

Brannan et al., "Summary Report—Investigations on reaction products of mufti-functional PEG derivatives," Baxter Healthcare Corporation, Nov. 13, 2009 (8 pages).

Chen et al. (1981), "Properties of two urate oxidases modified by the covalent attachment of poly(ethylene glycol)," *Biochem. Biophys. Acta.* 660:293-298.

Chvapil et al. (1969), "Some chemical and biological characteristics of a new collagen-polymer compound material," *J. Biomed. Mater. Res.* 3:315-332.

Coseal® Surgical Sealant, Instructions for Use, Baxter Healthcare Corporation, 21026 Alexander Court, Hayward, California 94545 (2 pages), 2011.

Davis et al. (1981), "Hypouricaemic effect of polyethyleneglycol modified urate oxidase," *Lancet* 2:281-283.

Doillon et al., "Collagen-based wound dressings: Control of the pore structure and morphology," *J. Biomed. Mat. Res.* 20(8):1219-1228, 1986.

Dreborg et al., "Immunotherapy with Monomethoxypolyethylene Glycol Modified Allergens," *Critical Reviews in Therapeutic Drug Carrier Systems* 6(4): 315-365, 1990.

Farouk et al., "Preliminary Experience with Butyl-2-Cyanoacrylate Adhesive in Tension-Free Inguinal Hernia Repair," *British Journal of Surgery* 83(8): 1100, Aug. 1996.

Ferruti (1981), "Succinic half-esters of poly(ethylene glycol)s and their benzotriazole and imidazole derivatives as oligomeric drug-binding matrices," *Makromol. Chem.* 182:2183-2192.

Fleisher et al. (1987), "Regeneration of lost attachment apparatus in the dog using polygalactin-910," *J. Dent. Res.* 281(66 spec.), Abstract No. 1393.

Gander et al. (1988), "Crosslinked poly(alkylene oxides) for the preparation of controlled release micromatrices," *J. Controlled Release* 5:271-283.

Gnanou et al. (1984), "Hydrophilic polyurethane networks based on poly(ethylene oxide): Synthesis, characterization, and properties. Potential applications as biomaterials," *Macromolecules* 17:945-952.

Gomel et al. (1992), "Infertility surgery: Microsurgery," *Current Opinion in Obstetrics and Gynecology* 4:390-399.

Goussous, "Effectiveness of the Mesh Plug Technique," *Surgery* 117(1): 600, 1995.

Harris, ed., in "Poly(Ethylene Glycol) Chemistry: Biotechnical & Biomedical Applications," Chapter 22, Plenum Press, NY (1992).

Hendrikx et al., "Evaluation of a Novel Synthetic Sealant for Inhibition of Cardiac Adhesions and Clinical Experience in Cardiac Surgery Procedures," The Heart Surgery Forum #2001-58921 4(3): 204-210, 2001.

Hoffmann et al., "Choice of Hemostatic Agent Influences Adhesion Formation in a Rat Cecal Adhesion Model," *Journal of Surgical Research* 155: 77-81, Jul. 2009.

Inada et al. (1984), "Ester synthesis catalyzed by polyethylene glycol-modified lipase in benzene," *Biochem. & Biophys. Res. Comm.* 122:845-850.

(56) References Cited

OTHER PUBLICATIONS

Jourdan et al., "Initial Experience with the Use of N-Butyl-2-Cyanoacrylate Glue for the Fixation of Polypropylene Mesh in Laparoscopic Hernia Repair," *Surgical Laparoscopy &Endoscopy* 8(4): 291-293, Aug. 1998.
Katkhouda et al., "Use of Fibrin Sealant for Prosthetic Mesh Fixation in Laparoscopic Extra peritoneal Inguinal Hernia Repair," *Annals of Surgery* 233(1): 18-25, 2001.
Katre et al. (1987), "Chemical modification of recombinant interleukin 2 by polyethylene glycol increases its potency in the murine meth A sarcoma model," *Proc. Natl. Acad. Sci.* USA 84:1487-1491.
Kroschwitz, *Concise Encyclopedia of Polymer Science and Engineering*, Wiley Intersciences Edition, New York, NY, p. 489, 1990.
Lerner et al., "Current Status of Surgical Adhesives," *Journal of Surgical Research* 48(2):165-181 (1990).
Lichtenwalner et al., *Encyclopedia of Polymer Science and Technology* 12: 535, eds. Mark, Gaylord and Bikales, John Wiley, New York, NY, 1970.
McPherson et al. (1988), "The influence of heparin on the wound healing response to collagen implants in vivo," *Collagen and Related Research Clinical and Experimental* 8(1):83-100.
Mettler et al., "A safety and efficacy study of a resorbable hydrogel for reduction of post-operative adhesions following myomectomy," *Human Reproduction* 23(5): 1093-1100, 2008.
Nakayama et al., "Photocurable Surgical Tissue Adhesive Glues Composed of Photoreactive Gelatin and Poly(Ethylene Glycol) Diacrylate," *Journal of Biomedical Materials Research (Applied Biomaterials)* 48(4): 511-521, 1999.
Nathan et al. (1993), "Copolymers of lysine and polyethylene glycol: A new family of functionalized drug carriers," *Bioconjugate Chem.* 4:54-62.
Nishida et al. (1984), "Hypouricaemic effect after oral administration in chickens of polyethylene glycol-modified uricase entrapped in liposomes," *J. Pharm. Pharmacol.* 36:354-355.
Ouchi et al., "Synthesis of 5-Fluorouracil-Terminated Monomethoxypoly(Ethylene Glycol)s, Their Hydrolysis Behavior, and Their Antitumor Activities," *Journal of Macromolecular Science-Chemistry A24*(9): 1011-1032, 1987.
Pados et al. (1992), "Adhesions," *Current Opinion in Obstetrics and Gynecology* 4:421-428.
Pagidas et al. (1992), "Effects of ringer's lactate, interceed (TC7) and gore-tex surgical membrane on postsurgical adhesion formation," *Fertility and Sterility* 57(1):199-201.
Pfannemüller and Emmerling, "Chemische Modifizierung der Starkeoberflach," *Starch* 35(9):298-303 (1983) (Abstract).
Prior et al., "A Sprayable Hemostat Containing Fibrillar Collagen, Bovine Thrombin, and Autologous Plasma," *Annual of Thoracic Surgery* 68: 479-485, 1999.
Pyatak et al. (1980), "Preparation of a polyethylene glycol: superoxide dismutase adduct, and an examination of its blood circulating life and anti-inflammatory activity," *Res. Com. Chem. Path. Pharmacol.* 29:113-127.
Ramshaw et al. (1984), "Precipitation of collagens by polyethylene glycols," *Anal. Biochem.* 141:361-365.
Savoca et al. (1979), "Preparation of a non-immunigenic arginase by the covalent attachment of polyethylene glycol," *Biochem. Biophys. Acta.* 578:47-53 (1979).

Sawhney et al. (1994), "Optimization of photopolymerized bioerodible hydrogel properties for adhesion prevention," *J. Biomed. Mat. Res.* 28:831-838.
Shaoe et al., "The Synthesis of N-benzyl-N-[3-(4-dhiorophenoxy)-2-hydroxypropyl] Glycine (NBG-CGE) and its Adhesive Mechanism with Hard Tooth Tissues," ACTA Academiac Medicinae Sichuan 13(3):248-54 (1982) (in Chinese w/English abstract).
Sperinde et al. (1997), "Phase transformation poly(ethylene glycol) hydrogels for tissue engineering and cell therapies," $23^{rd}$ *Annual Meeting of the Society for Biomaterials*, p. 247.
Steinleitner et al. (1991), "Poloxamer 407 as an intraperitoneal barrier material for the prevention of postsurgical adhesion formation and reformation in rodent models for reproductive surgery," *Obstetrics and Gynecology* 77:48-52.
Swenson, Wade T. And Nicolas Kowanko, *Cross-linked Polymers as Tissue Adhesives*, Abstracts of Papers of the American Chemical Society 205(part 1):239-CHED (1993).
Takahashi et al. (1984), "A chemical modification to make horseradish peroxidase soluble and active in benzene," *Biochem. & Biophys. Res. Comm.* 121:261-265.
Tulandi (1991), "Effects of fibrin sealant on tubal anastomosis and adhesion formation," *Fertility and Sterility* 56(1):136-138.
Ulbrich et al. (1986), "Poly(ethylene glycol)s containing enzymatically degradable bonds," *Makromol. Chem.* 187:1131-1144.
Urman et al. (1991), "Effect of hyaluronic acid on postoperative intraperitoneal adhesion formation and reformation in the rat model," *Fertility and Sterility* 56(3):568-570.
Viau et al. (1986), "Safety evaluation of free radical scavengers PEG-catalase and PEG-superoxide dismutase," *J. Free Rad. In Bio. & Med.* 2:283-288.
Viau et al. (1986), "Toxicologic studies of a conjugate of asparaginase and polyethylene glycol in mice, rats and dogs," *Am. J. Vet. Res.* 47:1398-1401.
Wallace et al., "A Tissue Sealant Based on Reactive Multifunctional Polyethylene Glycol," *Journal of Biomedical Materials Research (Applied Biomaterials)* 58: 545-555, 2001.
West et al. (1995), "Comparison of covalently and physically cross-linked polyethylene glycol-based hydrogels for the prevention of postoperative adhesions in a rat model," *Biomaterials* 16:1153-1156.
Wieder et al. (1979), "Some properties of polyethylene glycol: Phenylalanine ammonia-lyase adducts," *J. Biol. Chem.* 254:12579-12587.
Zalipsky et al., "Attachment of Drugs to Polyethylene Glycols," *Eur. Polym. J.* 19(12): 1177-1183, 1983.
Zalipsky et al., "A Convenient General Method for Synthesis of $N^{\alpha}$- or $N^{\omega}$-Dithiasuccinoyl (Dts) Amino Acids and Dipeptides: Application of Polyethylene Glycol as a Carrier for Functional Purification," *International Journal of Peptide Protein Research* 30: 740-783, 1987.
Zheng et al., "Production of Microspheres with Surface Amino Groups from Blends of Poly(Lactide-co-Glycolide) and Poly($\epsilon$-CBZ-L-Lysine) and Use for Encapsulation," *Biotechnol. Progr.* 15: 763-767, 1999.
Zieren et al., "Is Mesh Fixation Necessary in Abdominal Hernia Repair?," *Langenbeck's Arch Surg.* 384: 71-75, 1999.
U.S. Appl. No. 08/573,799, filed Dec. 18, 1995 (Rhee et al.).
U.S. Appl. No. 09/649,337, filed Aug. 28, 2000 (Wallace et al.).
U.S. Appl. No. 09/733,739, filed Dec. 8, 2000 (Rhee et al.).

\* cited by examiner

ADHESIVE TISSUE REPAIR PATCH AND COLLAGEN SHEETS

CROSS-REFERENCE TO RELATED APPLICATIONS

This application is a continuation of U.S. application Ser. No. 10/971,684, filed Oct. 22, 2004, which is a divisional application of U.S. application Ser. No. 10/262,640, filed Sep. 30, 2002, now U.S. Pat. No. 6,833,408, which is a continuation-in-part of U.S. application Ser. No. 09/883,138, filed Jun. 15, 2001, now U.S. Pat. No. 6,458,889, which is a continuation-in-part of U.S. application Ser. No. 09/649,337, filed Aug. 28, 2000, now U.S. Pat. No. 6,495,127, claiming the benefit under 35 U.S.C. §119(e) of U.S. Provisional Application Ser. No. 60/151,273, filed Aug. 27, 1999, which applications are incorporated herein by reference in their entireties.

BACKGROUND

1. Technical Field

This invention relates generally to methods for repairing tissue using adhesive compositions comprised of a hydrophilic polymer and crosslinked biomaterials. More specifically, the invention relates to tissue repair using a composition of collagen and crosslinkable components.

2. Description of the Related Art

Tissue damage can result from many causes. Examples of such causes include surgical incisions, such as internal and epidermal surgical incisions; prosthetic implants, including injury attendant surgery such as hip replacements; and wounds, including lacerations, incisions, and penetrations. Often such damage is the result of herniation wherein the outer layers of the abdominal wall weaken, tear, or bulge. The resulting weakened area or hole allows for sections of the inner lining of the abdominal cavity, or peritoneum, to protrude. This protrusion can be painful and if uncorrected can result in strangulation of the protruding tissue. Although almost all tissue can become herniated, the tissue in the inguinal canal, in the navel, and surrounding the location of former incisions are most common. Since the early 1980's, the surgical techniques used in repairing inguinal or groin hernias have undergone a profound transformation. One such technique incorporates a surgically acceptable patch as part of the groin hernia repair. Goussous, "Effectiveness of The Mesh Plug Technique" (letter), *Surgery* 117:600 (1995). Over time, scar tissue forms around the reinforcing mesh, creating a supporting wall to minimize future hernias.

Various methods for approaching the herniated tissue and affixing the mesh prosthesis have been developed. There are two primary techniques used in hernia repair. In the traditional "open surgery" technique, the surgeon makes a three- to four-inch incision in the abdominal wall, pushes the hernial sac inside, and uses mesh to reinforce the abdominal wall. The other method of hernia repair is the laparoscopic technique, wherein three tiny incisions, about the size of dime, provide the surgeon sufficient access to reposition the hernia sac back through its hole and secure a mesh patch over the weak area in the muscle wall. The incisions used in the laparoscopic technique are sufficiently small so that they can be covered by adhesive strips and there is minimal or no scarring.

The surgically acceptable patch used in both of the above-discussed techniques is generally held in place via suturing or stapling to the surrounding tissue. Unfortunately, the use of such sutures or staples may increase the patient's discomfort and increase the incidences of wound infection, vascular injury, and entrapment neuropathy. While herniorrhaphies have been conducted without firmly connecting the patch to the tissue surface and allowing the pressure of the peritoneum to hold the patch against the posterior side of the abdominal wall, see Zieren et al., "Is Mesh Fixation Necessary in Abdominal Hernia Repair?" *Lang. Arch Surg.* 384:71-75 (1999), fixation of the patch is generally preferred in order to avoid folding, shrinkage, and migration of the patch and is usually considered to be essential in laparoscopic procedures.

Recently cyanoacrylates and fibrin glues have been used as fixatives in hernia repair. While Katkhouda et al., *Ann. Surg.* 233:18-25 (2001) present the use of a fibrin sealant as a patch fixative, such fibrin products are made from human products and are thus susceptible to contamination. In addition, fibrin adhesives are difficult to prepare and to store. The use of cyanoacrylates as adhesives also presents problems in that the adhesive may not be biocompatible and may not provide a sufficient degree of elasticity thereby resulting in increased patient discomfort and an increased incidence of reoccurrence. See Farouk et al., "Preliminary Experience with utyl-2-Cyanoacrylate adhesive in Tension-Free Inguinal Hernia Repair," *Brit. J. Surg.* 83:1100 (1996) and Jourdan et al., "The Use of N-Butyl-2-Cyanoacrylate Glue for the Fixation of Polypropylene Mesh in Laparoscopic Hernia Repair," *6th World Cong. of Endo. Surg.*, 1221-1225 (1998).

A new method of tissue repair has now been developed using a surgically acceptable hydrophilic-based crosslinking adhesive. The use of this adhesive composition avoids the potential complications inherent in suture or staple based methods of tissue attachment. In addition, as the hydrophilic polymer-based adhesive does not contain human blood products, the danger of contamination present with fibrin adhesives is removed. While providing a stronger adhesive bond than fibrin adhesives such as TISSEEL®, the hydrophilic polymer-based crosslinking adhesive is much more flexible than cyanoacrylate adhesives and is completely biocompatible.

U.S. Pat. No. 5,162,430, to Rhee et al., and commonly owned by the assignee of the present invention, discloses collagen-synthetic polymer conjugates prepared by covalently binding collagen to synthetic hydrophilic polymers such as various derivatives of polyethylene glycol.

Commonly owned U.S. Pat. No. 5,324,775, to Rhee et al., discloses various inert, naturally occurring, biocompatible polymers (such as polysaccharides) covalently bound to synthetic, hydrophilic polyethylene glycol polymers.

Commonly owned U.S. Pat. No. 5,328,955, to Rhee et al., discloses various activated forms of polyethylene glycol and various linkages which can be used to produce collagen-synthetic polymer conjugates having a range of physical and chemical properties.

Commonly owned, U.S. application Ser. No. 08/403,358, filed Mar. 14, 1995, now abandoned, a European counterpart of which was published as EP 96102366, discloses a crosslinked biomaterial composition that is prepared using a hydrophobic crosslinking agent, or a mixture of hydrophilic and hydrophobic crosslinking agents. Preferred hydrophobic crosslinking agents include any hydrophobic polymer that contains, or can be chemically derivatized to contain, two or more succinimidyl groups.

Commonly owned U.S. Pat. No. 5,580,923 to Yeung et al., discloses a composition useful in the prevention of surgical adhesions. The composition has a substrate, which is preferably collagen and a binding agent, which preferably has at least one tissue-reactive functional group and at least one substrate-reactive functional group.

Commonly owned U.S. Pat. No. 5,614,587 to Rhee et al., discloses bioadhesive compositions having collagen crosslinked using a multifunctionally activated synthetic hydrophilic polymer, as well as methods of using such compositions to effect adhesion between a first surface and a second surface. At least one of the first and second surfaces is preferably a native tissue surface.

Japanese patent publication No. 07090241 discloses a composition used for temporary adhesion of a lens material to a machining device, which contains a mixture of polyethylene glycol, having an average molecular weight in the range of 1000-5000, and poly-N-vinylpyrrolidone, having an average molecular weight in the range of 30,000-200,000.

West and Hubbell, *Biomaterials* 16:1153-1156 (1995), disclose the prevention of post-operative adhesions using a photopolymerized polyethylene glycol-co-lactic acid diacrylate hydrogel and a physically crosslinked polyethylene glycol-co-polypropylene glycol hydrogel, Poloxamer 407®.

Each publication cited above is incorporated herein by reference to describe and disclose the subject matter for which it is cited.

The invention is directed to a method of repairing tissue, such as herniated tissue, using a versatile biocompatible adhesive composition not previously disclosed or envisioned by those in the biomaterial field. The composition has a hydrophilic polymer and crosslinkable components that may be readily crosslinked upon admixture with an aqueous medium to provide a crosslinked composition suitable for use as a bioadhesive. The adhesive composition is biocompatible, and does not leave any toxic, inflammatory, or immunogenic reaction products at the site of administration. Preferably, the composition is not subject to enzymatic cleavage by matrix metalloproteinases such as collagenase, and is therefore not readily degradable in vivo. As a result, the adhesive composition will degrade more slowly than either the hydrophilic polymer component or the crosslinkable component as the two components will serve to mutually protect each other from the effects of metalloproteases or hydrolysis.

BRIEF SUMMARY

Accordingly, in one aspect of the invention, a method for tissue repair is provided utilizing a readily crosslinkable, biocompatible, adhesive composition to secure a surgically acceptable patch to the damaged tissue. The adhesive composition is comprised of a hydrophilic polymer, a crosslinkable component A having m nucleophilic groups, wherein m≥2; and a crosslinkable component B having n electrophilic groups capable of reaction with the m nucleophilic groups to form covalent bonds, wherein n≥2 and m+n≥4. In the composition, each of components A and B is biocompatible and nonimmunogenic, at least one of components A and B is a hydrophilic polymer, and admixture of components A and B in an aqueous medium result in crosslinking of the composition to give a biocompatible, nonimmunogenic, crosslinked matrix.

Each of the crosslinkable components may be polymeric, in which case at least two crosslinkable components are generally although not necessarily composed of a purely synthetic polymer rather than a naturally occurring or semi-synthetic polymer, wherein "semi-synthetic" refers to a chemically modified naturally occurring polymer. Alternatively, one or two of crosslinkable components A and B may be a low molecular weight crosslinking agent, typically an agent comprised of a hydrocarbyl moiety containing 2 to 14 carbon atoms and at least two functional groups, i.e., nucleophilic or electrophilic groups, depending on the component.

For convenience, the term "polynucleophilic" will be used herein to refer to a compound having two or more nucleophilic moieties, and the term "polyelectrophilic" will be used to refer to a compound having two or more electrophilic moieties. The adhesive composition may also additionally comprise an optional third biocompatible and nonimmunogenic crosslinkable component C having at least one functional group selected from (i) nucleophilic groups capable of reacting with the electrophilic groups of component B and (ii) electrophilic groups capable of reacting with the nucleophilic groups of component A.

Any conventional surgical procedure may be used to access the herniated tissue and any conventional surgically acceptable patch may be affixed with the adhesive composition. For example, a polypropylene patch may be affixed to the posterior surface of the abdominal wall via laparoscopic surgical techniques or may be affixed to the anterior surface via open surgical techniques. The method if applicable to a wide variety of hernia types, including, but not limited to, inguinal hernias, femoral hernias, scrotal hernias, ventral hernias, umbilical hernias, ventral/epigastric hernias, incisional hernias, spigelian hernias, recurrent hernias, recurrent incisional hernias, bilateral hernias, stoma hernias, and hiatus hernias.

In another aspect of the invention, a kit is provided comprising the adhesive composition as discussed above and a surgically acceptable patch.

In a still further aspect of the invention, a pretreated patch is provided comprising a surgically acceptable patch that has been coated with the adhesive composition as discussed above.

BRIEF DESCRIPTION OF THE DRAWINGS

In FIGS. 1-10, the polyelectrophilic components have four hydroxyl groups substituted with PEG, and with each PEG branch terminated with a reactive electrophilic group.

DETAILED DESCRIPTION

Definitions and Nomenclature

Figure 1:
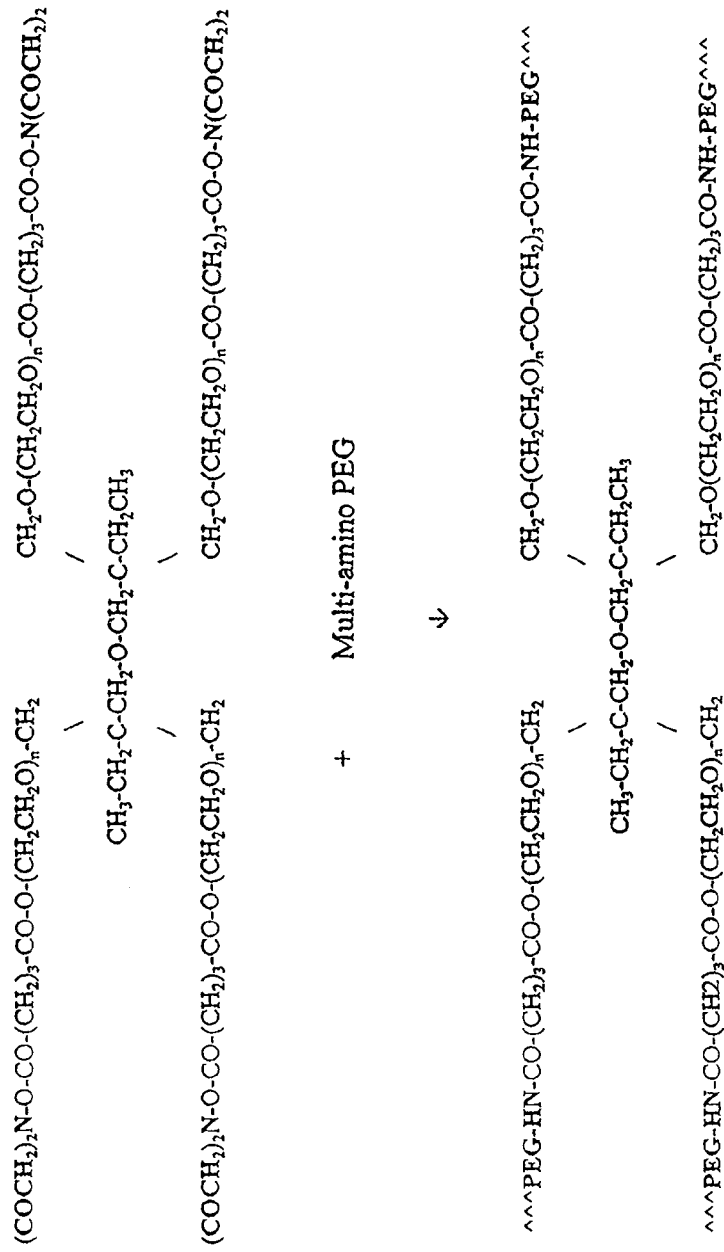
FIGS. 1 to 10 schematically illustrate reaction of various polyelectrophilic components with substituted polyethylene glycol (PEG) as a representative polynucleophile.

Before describing the present invention in detail, it is to be understood that unless otherwise indicated this invention is not limited to particular compositional forms, crosslinkable components, crosslinking techniques, or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a crosslinkable component" refers not only to a single crosslinkable component but also to a combination of two or more different crosslinkable components, "a hydrophilic polymer" refers to a combination of hydrophilic polymers as well as to a single hydrophilic polymer, and the like.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. All patents, patent applications and other publications mentioned herein are incorporated herein by reference. Specific terminology of particular importance to the description of the present invention is defined below.

As used herein, the terms "bioadhesive", "biological adhesive", and "surgical adhesive" are used interchangeably to refer to biocompatible compositions capable of effecting temporary or permanent attachment between the surfaces of two native tissues, or between a native tissue surface and either a non-native tissue surface or a surface of a synthetic implant.

The term "surgically acceptable" refers to those items, e.g., patches, that are biocompatible, and are otherwise acceptable for surgical use.

The term "crosslinked" herein refers to a composition containing intermolecular crosslinks and optionally intramolecular crosslinks as well, arising from the formation of covalent bonds. Covalent bonding between two crosslinkable components may be direct, in which case an atom in one component is directly bound to an atom in the other component, or it may be indirect, through a linking group. A crosslinked matrix may, in addition to covalent bonds, also include intermolecular and/or intramolecular noncovalent bonds such as hydrogen bonds and electrostatic (ionic) bonds. The term "crosslinkable" refers to a component or compound that is capable of undergoing reaction to form a crosslinked composition.

The terms "nucleophile" and "nucleophilic" refer to a functional group that is electron rich, has an unshared pair of electrons acting as a reactive site, and reacts with a positively charged or electron-deficient site, generally present on another molecule.

The terms "electrophile" and "electrophilic" refer to a functional group that is susceptible to nucleophilic attack, i.e., susceptible to reaction with an incoming nucleophilic group. Electrophilic groups herein are positively charged or electron-deficient, typically electron-deficient.

The term "activated" refers to a modification of an existing functional group to generate or introduce a new reactive functional group from the prior existing functional group, wherein the new reactive functional group is capable of undergoing reaction with another functional group to form a covalent bond. For example, a component containing carboxylic acid (—COOH) groups can be activated by reaction with N-hydroxysuccinimide or N-hydroxysulfo-succinimide using known procedures, to form an activated carboxylate (which is a reactive electrophilic group), i.e., an N-hydroxysuccinimide ester or an N-hydroxysulfosuccinimide ester, respectively. In another example, carboxylic acid groups can be activated by reaction with an acyl halide, e.g., an acyl chloride, again using known procedures, to provide an activated electrophilic group in the form of an anhydride.

The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about –0.5, where P is the partition coefficient of the compound between octanol and water, while hydrophobic compounds will generally have a log P greater than about 3.0, typically greater than about 5.0. Preferred crosslinkable components herein are hydrophilic, although as long as the crosslinkable composition as a whole contains at least one hydrophilic component, crosslinkable hydrophobic components may also be present.

The term "polymer" is used not only in the conventional sense to refer to molecules composed of repeating monomer units, including homopolymers, block copolymers, random copolymers, and graft copolymers, but also, as indicated in parent application Ser. No. 09/733,739, now U.S. Pat. No. 6,323,728, to refer to polyfunctional small molecules that do not contain repeating monomer units but are "polymeric" in the sense of being "polyfunctional," i.e., containing two or more functional groups. Accordingly, it will be appreciated that when the term "polymer" is used, difunctional and polyfunctional small molecules are included. Such moieties include, by way of example: the difunctional electrophiles disuccinimidyl suberate (DSS), bis(sulfosuccinimidyl) suberate ($BS^3$), dithiobis(succinimidylpropionate) (DSP), bis(2-succinimidooxy-carbonyloxy)ethyl sulfone (BSOCOES), 3,3'-dithiobis(sulfosuccinimidylpropionate (DTSSP); and the di- and polyfunctional nucleophiles ethylenediamine ($H_2N$—$CH_2$—$CH_2$—$NH_2$), tetramethylene diamine ($H_2N$—$[CH_2]_4$—$NH_2$), pentamethylene diamine (cadaverine) ($H_2N$—$[CH_2]_5$—$NH_2$), hexamethylene diamine ($H_2N$—$[CH_2]_6$—$NH_2$), bos(2-aminoethyl)amine (HN—$[CH_2$—$CH_2$—$NH_2]_2$), and tris (2-aminoethyl)amine (N—$[CH_2$—$CH_2$—$NH_2]_3$). All suitable polymers herein are nontoxic, non-inflammatory, and nonimmunogenic, and will preferably be essentially nondegradable in vivo over a period of up to 30 days in vivo.

The term "synthetic" to refer to various polymers herein is intended to mean "chemically synthesized." Therefore, a synthetic polymer in the present compositions may have a molecular structure that is identical to a naturally occurring polymer, but the polymer per se, as incorporated in the compositions of the invention, has been chemically synthesized in the laboratory or industrially. "Synthetic" polymers also include semi-synthetic polymers, i.e., naturally occurring polymers, obtained from a natural source, that have been chemically modified in some way. Generally, however, the synthetic polymers herein are purely synthetic, i.e., they are neither semi-synthetic nor have a structure that is identical to that of a naturally occurring polymer.

The term "synthetic hydrophilic polymer" as used herein refers to a synthetic polymer composed of molecular segments that render the polymer as a whole "hydrophilic," as defined above. Preferred polymers are highly pure or are purified to a highly pure state such that the polymer is or is treated to become pharmaceutically pure. Most hydrophilic polymers can be rendered water-soluble by incorporating a sufficient number of oxygen (or less frequently nitrogen) atoms available for forming hydrogen bonds in aqueous solutions. Hydrophilic polymers useful herein include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly(ethyloxazoline); and polyvinylamines.

Hydrophobic polymers, including low molecular weight polyfunctional species, can also be used in the crosslinkable compositions of the invention. Hydrophobic polymers preferably contain, or can be derivatized to contain, two or more electrophilic groups, such as succinimidyl groups, most preferably, two, three, or four electrophilic groups. Generally, "hydrophobic polymers" herein contain a relatively small proportion of oxygen and/or nitrogen atoms. Preferred hydrophobic polymers for use in the invention generally have a carbon chain that is no longer than about 14 carbons. Polymers having carbon chains substantially longer than 14 carbons generally have very poor solubility in aqueous solutions and, as such, have very long reaction times when mixed with aqueous solutions of synthetic polymers containing multiple nucleophilic groups.

The term "collagen" as used herein refers to all forms of collagen, including those, which have been processed or otherwise modified. Preferred collagens do not posses telopeptide regions ("atelopeptide collagen"), are soluble, and may be in fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may also be used to form particularly rigid crosslinked compositions. Collagen used in connection with the preferred embodiments of the invention is in a pharmaceutically pure form such that it can be incorporated into a human body for the intended purpose.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "cytokine" is used to describe biologically active molecules including growth factors and active peptides, which aid in healing or regrowth of normal tissue. The function of cytokines is two-fold: 1) they can incite local cells to produce new collagen or tissue, or 2) they can attract cells to the site in need of correction. As such, cytokines serve to encourage "biological anchoring" of the collagen implant within the host tissue. As previously described, the cytokines can either be admixed with the collagen-polymer conjugate or chemically coupled to the conjugate. For example, one 30 may incorporate cytokines such as epidermal growth factor (EGF), transforming growth factor (TGF)-α, TGF-β (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, tumor necrosis factors (TNF), interleukins, colony stimulating factors (CSFs), erythropoietin (EPO), nerve growth factor (NGF), interferons (IFN) bone morphogenic protein (BMP), osteogenic factors, and the like. Incorporation of cytokines, and appropriate combinations of cytokines can facilitate the regrowth and remodeling of the implant into normal bone tissue, or may be used in the treatment of wounds.

The term "effective amount" refers to the amount of composition required in order to obtain the effect desired. Thus, a "tissue growth-promoting amount" of a composition refers to the amount needed in order to stimulate tissue growth to a detectable degree. Tissue, in this context, includes connective tissue, bone, cartilage, epidermis and dermis, blood, and other tissues. The actual amount that is determined to be an effective amount will vary depending on factors such as the size, condition, sex, and age of the patient and can be more readily determined by the caregiver.

The term "suitable fibrous material" as used herein, refers to a fibrous material which is substantially insoluble in water, non-immunogenic, biocompatible, and immiscible with the crosslinkable compositions of the invention. The fibrous material may comprise any of a variety of materials having these characteristics and may be combined with crosslinkable compositions herein in order to form and/or provide structural integrity to various implants or devices used in connection with medical and pharmaceutical uses. For example, the crosslinkable compositions of the invention can be coated on the "suitable fibrous material," which can then be wrapped around a bone to provide structural integrity to the bone. Thus, the "suitable fibrous material" is useful in forming the "solid implants" of the invention.

The term "in situ" as used herein means at the site of administration. Thus, the injectable reaction mixture compositions are injected or otherwise applied to a specific site within a patient's body, e.g., the locus of the herniated tissue, and allowed to crosslink at the site of injection.

The term "aqueous medium" includes solutions, suspensions, dispersions, colloids, and the like containing water.

The term "substantially immediately" means within less than five minutes, preferably within less than two minutes, and the term "immediately" means within less than one minute, preferably within less than 30 seconds.

The terms "active agent," and "biologically active agent" are used interchangeably herein to refer to a chemical material or compound suitable for administration to a patient and that induces a desired effect. The terms include agents that are therapeutically effective as well as prophylactically effective. Also included are derivatives and analogs of those compounds or classes of compounds specifically mentioned that also induce the desired effect.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

With regard to nomenclature pertinent to molecular structures, the following definitions apply:

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups. "Alkylene," "lower alkylene" and "substituted alkylene" refer to divalent alkyl, lower alkyl, and substituted alkyl groups, respectively.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. The terms "arylene" and "substituted arylene" refer to divalent aryl and substituted aryl groups as just defined.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. If not otherwise indicated, "hydrocarbyl" indicates unsubstituted hydrocarbyl, substituted hydrocarbyl, heteroatom-containing hydrocarbyl, and substituted heteroatom-containing hydrocarbyl. Unless otherwise indicated, the terms "hydrocarbyl" and "hydrocarbylene" include substituted hydrocarbyl and substituted hydrocarbylene, heteroatom-containing hydrocarbyl and heteroatom-containing hydrocarbylene, and substituted heteroatom-containing hydrocarbyl and substituted heteroatom-containing hydrocarbylene, respectively.

By "substituted" as in "substituted hydrocarbyl," "substituted alkyl," and the like, as alluded to in some of the aforementioned definitions, is meant that in the hydrocarbyl, alkyl, or other moiety, at least one hydrogen atom bound to a carbon atom is replaced with one or more substituents that are functional groups such as alkoxy, hydroxy, halo, nitro, and the like. Unless otherwise indicated, it is to be understood that specified molecular segments can be substituted with one or more substituents that do not compromise a compound's utility. For example, "succinimidyl" is intended to include unsubstituted succinimidyl as well as sulfosuccinimidyl and other succinimidyl groups substituted on a ring carbon atom, e.g., with alkoxy substituents, polyether substituents, or the like.

Repair of Damaged Tissue

While the adhesive composition taught herein may be used in any number of tissue repair applications, such as, but not limited to, seroma and hematoma prevention, skin and muscle flap attachment, repair and prevention of endoleaks, aortic dissection repair, lung volume reduction, neural tube repair and the making of microvasuclar and neural anastomoses, the focus of the invention is the use of the adhesive composition in the repair of damaged tissue.

In the method of the invention, the repair of damaged tissue may be carried out within the context of any standard surgical process allowing access to and repair of the tissue, including open surgery and laparoscopic techniques. Once the damaged tissue is accessed, the adhesive composition of the invention is placed in contact with the damaged tissue along with any surgically acceptable patch or implant, if needed. When used to repair lacerated or separated tissue, such as by joining two or more tissue surfaces, the adhesive composition is applied to one or more of the tissue surfaces and then the surfaces are placed in contact with each other and adhesion occurs therebetween.

When used to repair herniated tissue, a surgically acceptable patch can be attached to the area of tissue surrounding the herniated tissue so as to cover the herniated area, thereby reinforcing the damaged tissue and repairing the defect. When attaching the patch to the surrounding tissue, the adhesive composition may be applied to either the patch, to the surrounding tissue, or to the patch after the patch has been placed on the herniated tissue. Once the patch and tissue are brought into contact with each other, adhesion occurs therebetween.

Preferably, all reactive components of the adhesive composition are first mixed to initiate crosslinking, then delivered to the desired tissue or surface before substantial crosslinking has occurred. The surface or tissue to which the adhesive composition has been applied is then contacted with the remaining surface, i.e. another tissue surface or implant surface, preferably immediately, to effect adhesion.

The surfaces to be adhered may be held together manually, or using other appropriate means, while the crosslinking reaction is proceeding to completion. Crosslinking is typically sufficiently complete for adhesion to occur within about 5 to 60 seconds after mixing the components of the adhesive composition. However, the time required for complete crosslinking to occur is dependent on a number of factors, including the type and molecular weight of each reactive component, the degree of functionalization, and the concentration of the components in the crosslinkable compositions (e.g., higher component concentrations result in faster crosslinking times).

Surgically Acceptable Patches

When the adhesive composition of the invention is used to repair damaged tissue, it may be used in conjunction with a surgically acceptable patch. The surgically acceptable patch may be selected from any conventional patch type that is suitable for use in hernia repair. Many types of patches are currently available and will be well know to one of skill in the art. Exemplary patch materials include nonabsorbable materials such as tantalum mesh, stainless steel mesh, polyester cloth, polyester sheeting, nylon mesh, Dacron mesh, acrylic cloth, polyvinyl sponge, polytetrafluoroethylene (PTFE), expanded PTFE, polyvinyl cloth, polypropylene mesh. Of these, polypropylene mesh, commercially available as MAR-LEX® (Phillips Petroleum Company, Bartlesville, Okla.) or PROLENE® (Ehticon, Inc., Somerville, N.J.), is preferred. Exemplary absorbable meshes include collagen, polyglycolic acid, polyglactin, and carbon fiber mesh.

The patch may be in the form of a single flat sheet or may be folded into a "plug" as is customarily used in tension free hernia repair methods. Plug/patch combinations are also suitable for use with the adhesive composition. For example, the Prolene Hernia System™ (Ethicon, Somerville, N.J.), uses two sheets of polypropylene joined at a center plug that are placed against the anterior and posterior surfaces of the herniated abdominal wall with the center plug passing through the area of herniation. Other types of acceptable patches are well known to one of skill in the art. U.S. Pat. No. 6,258,124 to Darois, U.S. Pat. No. 5,147,374 to Fernadex, and U.S. Pat. No. 5,176,692 to Wilk et al. disclose several variations of hernia repair patches and methods.

The density, porosity, permeability, and thickness of the patch will vary for different patch types and different surgical applications. In general, a clean, dry, non-oily, rough surface is preferred. The patch need not be functionalized as the patch may be entrapped in the adhesive composition matrix that is bound to the tissue surface. If desired, the patch may however be functionalized with nucleophilic groups such as, but not limited to, amines, sulfhydryls, and the like. Such functional groups may serve to enhance the bonding strength of the adhesive composition. The patch may also be coated with the adhesive composition components in dry form. When such a coated patch is used, the adhesive composition begins to crosslink once exposed to moisture, such as body fluids, and so forth.

Administration and Use

The adhesive compositions of the present invention may be applied to any tissue surface and may be used in any customary method of tissue repair. The adhesive composition, as discussed below, is preferably applied before crosslinking of the various components of the composition has reached "equilibrium." The point at which crosslinking has reached equilibrium is defined herein as the point at which the composition no longer feels tacky or sticky to the touch. The adhesive compositions of the present invention are generally delivered to the site of administration in such a way that the individual components of the composition come into contact with one another for the first time at the site of administration, or within one hour preceding administration.

Thus, in one embodiment the compositions of the present invention are delivered to the site of administration using an apparatus that allows the components to be delivered separately. Such delivery systems usually involve a multi-compartment spray device. Alternatively, the components can be delivered separately using any type of controllable extrusion system, or they can be delivered manually in the form of separate pastes, liquids or dry powders, and mixed together manually at the site of administration. Many devices that are adapted for delivery of multi-component tissue sealants/hemostatic agents are well known in the art and can also be used in the practice of the present invention.

Yet another way of delivering the adhesive compositions of the present invention is to prepare the reactive components in inactive form as either a liquid or powder. Such compositions can then be activated after application to the tissue site, or immediately beforehand, by applying an activator. In one embodiment, the activator is a buffer solution having a pH that will activate the composition once mixed therewith. Still another way of delivering the compositions is to prepare preformed sheets, and apply the sheets as such to the site of administration. One of skill in the art can easily determine the appropriate administration protocol to use with any particular composition having a known gel strength and gelation time. A more detailed description of the adhesive composition is given below.

The Adhesive Composition

The adhesive composition has a hydrophilic polymer component and a plurality of crosslinkable components. Additionally, other components may also be present. A discussion of each of these components is presented below.

The Hydrophilic Polymer component

The hydrophilic polymer component may be a synthetic or naturally occurring hydrophilic polymer. Naturally occurring hydrophilic polymers include, but are not limited to: proteins such as collagen, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen and glycosaminoglycans are preferred naturally occurring hydrophilic polymers for use herein.

In general, collagen from any source may be used in the adhesive composition of the method; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. Commonly owned U.S. Pat. No. 5,428,022, to Palefsky et al., discloses methods of extracting and purifying collagen from the human placenta. Commonly owned U.S. Pat. No. 5,667,839, to Berg, discloses methods of producing recombinant human collagen in the milk of transgenic animals, including transgenic cows. The term "collagen" or "collagen material"

as used herein refers to all forms of collagen, including those that have been processed or otherwise modified.

Collagen of any type, including, but not limited to, types I, II, III, IV, or any combination thereof, may be used in the compositions of the invention, although type I is generally preferred. Either atelopeptide or telopeptide-containing collagen may be used; however, when collagen from a source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the compositions of the invention, although previously crosslinked collagen may be used. Non-crosslinked atelopeptide fibrillar collagen is commercially available from McGhan Medical Corporation (Santa Barbara, Calif.) at collagen concentrations of 35 mg/mL and 65 mg/mL under the trademarks ZYDERM® I Collagen and ZYDERM® II Collagen, respectively. Glutaraldehyde-crosslinked atelopeptide fibrillar collagen is commercially available from McGhan Medical Corporation at a collagen concentration of 35 mg/mL under the trademark ZYPLAST®.

Collagens for use in the present invention are generally, although not necessarily, in aqueous suspension at a concentration between about 20 mg/mL to about 120 mg/mL, preferably between about 30 mg/mL to about 90 mg/mL.

Although intact collagen is preferred, denatured collagen, commonly known as gelatin, can also be used in the compositions of the invention. Gelatin may have the added benefit of being degradable faster than collagen.

Because of its greater surface area and greater concentration of reactive groups, nonfibrillar collagen is generally preferred. The term "nonfibrillar collagen" refers to any modified or unmodified collagen material that is in substantially nonfibrillar form at pH 7, as indicated by optical clarity of an aqueous suspension of the collagen.

Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII.

Chemically modified collagens that are in nonfibrillar form at neutral pH include succinylated collagen, propylated collagen, ethylated collagen, methylated collagen, and the like, both of which can be prepared according to the methods described in U.S. Pat. No. 4,164,559, to Miyata et al., which is hereby incorporated by reference in its entirety. Due to its inherent tackiness, methylated collagen is particularly preferred, as disclosed in commonly owned U.S. Pat. No. 5,614,587 to Rhee et al.

Collagens for use in the crosslinkable compositions of the present invention may start out in fibrillar form, then rendered nonfibrillar by the addition of one or more fiber disassembly agents. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them.

Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

As fibrillar collagen has less surface area and a lower concentration of reactive groups than nonfibrillar, fibrillar collagen is less preferred. However, as disclosed in commonly owned, U.S. application Ser. No. 08/476,825, now U.S. Pat. No. 5,614,587, fibrillar collagen, or mixtures of nonfibrillar and fibrillar collagen, may be preferred for use in adhesive compositions intended for long-term persistence in vivo, if optical clarity is not a requirement.

Synthetic hydrophilic polymers may also be used in the present invention. Useful synthetic hydrophilic polymers include, but are not limited to: polyalkylene oxides, particularly polyethylene glycol and poly(ethylene oxide)-polypropylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly (acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly (ethyloxazoline); and polyvinylamines. It must be emphasized that the aforementioned list of polymers is not exhaustive, and a variety of other synthetic hydrophilic polymers may be used, as will be appreciated by those skilled in the art.

The Crosslinkable Components

The adhesive composition also comprises a plurality of crosslinkable components. Each of the crosslinkable components participates in a reaction that results in a crosslinked matrix. Prior to completion of the crosslinking reaction, the crosslinkable components provide the necessary adhesive qualities that enable the method of the invention.

The crosslinkable components are selected so that crosslinking gives rise to a biocompatible, nonimmunogenic matrix useful in a variety of contexts other than the presently claimed method, including adhesion prevention, biologically active agent delivery, tissue augmentation, and other applications. The crosslinkable components of the invention comprise: a component A, which has m nucleophilic groups, wherein $m \geq 2$ and a component B, which has n electrophilic groups capable of reaction with the m nucleophilic groups, wherein $n \geq 2$ and $m+n \geq 4$. An optional third component, optional component C, which has at least one functional group that is either electrophilic and capable of reaction with the nucleophilic groups of component A or nucleophilic and capable of reaction with the electrophilic groups of component B may also be present. Thus, the total number of functional groups present on components A, B and C, when present, in combination is greater than or equal to 5; that is, the total functional groups given by m+n+p must be greater than or equal to 5, where p is the number of functional groups on component C and, as indicated, is greater than or equal to 1. Each of the components is biocompatible and nonimmunogenic, and at least one component is comprised of a hydrophilic polymer. In addition, as will be appreciated, the adhesive composition may contain additional crosslinkable components D, E, F, etc., having one or more reactive nucleophilic or electrophilic groups and thereby participate in formation of the crosslinked biomaterial via covalent bonding to other components.

The m nucleophilic groups on component A may all be the same, or, alternatively, A may contain two or more different nucleophilic groups. Similarly, the n electrophilic groups on component B may all be the same, or two or more different electrophilic groups may be present. The functional group(s) on optional component C, if nucleophilic, may or may not be the same as the nucleophilic groups on component A, and, conversely, if electrophilic, the functional group(s) on optional component C may or may not be the same as the electrophilic groups on component B.

Accordingly, the components may be represented by the structural formulae

 (I)

$R^1(-[Q^1]_q-X)_m$ (component A),

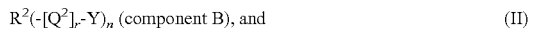 (II)

$R^2(-[Q^2]_r-Y)_n$ (component B), and

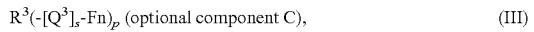 (III)

$R^3(-[Q^3]_s-Fn)_p$ (optional component C), wherein:

$R^1$, $R^2$ and $R^3$ are independently selected from the group consisting of $C_2$ to $C_{14}$ hydrocarbyl, heteroatom-containing $C_2$ to $C_{14}$ hydrocarbyl, hydrophilic polymers, and hydrophobic polymers, providing that at least one of $R^1$, $R^2$ and $R^3$ is a hydrophilic polymer, preferably a synthetic hydrophilic polymer;

X represents one of the m nucleophilic groups of component A, and the various X moieties on A may be the same or different;

Y represents one of the n electrophilic groups of component B, and the various Y moieties on A may be the same or different;

Fn represents a functional group on optional component C;

$Q^1$, $Q^2$ and $Q^3$ are linking groups;

$m \geq 2$, $n \geq 2$, m+n is $\geq 4$, q, and r are independently zero or 1, and when optional component C is present, $p \geq 1$, and s is independently zero or 1.

Reactive Groups

X may be virtually any nucleophilic group, so long as reaction can occur with the electrophilic group Y. Analogously, Y may be virtually any electrophilic group, so long as reaction can take place with X. The only limitation is a practical one, in that reaction between X and Y should be fairly rapid and take place automatically upon admixture with an aqueous medium, without need for heat or potentially toxic or non-biodegradable reaction catalysts or other chemical reagents. It is also preferred although not essential that reaction occur without need for ultraviolet or other radiation. Ideally, the reactions between X and Y should be complete in under 60 minutes, preferably under 30 minutes. Most preferably, the reaction occurs in about 5 to 15 minutes or less.

Examples of nucleophilic groups suitable as X include, but are not limited to, $-NH_2$, $-NHR^4$, $-N(R^4)_2$, $-SH$, $-OH$, $-COOH$, $-C_6H_4-OH$, $-PH_2$, $-PHR^5$, $-P(R^5)_2$, $-NH-NH_2$, $-CO-NH-NH_2$, $-C_5H_4N$, etc. wherein $R^4$ and $R^5$ are hydrocarbyl, typically alkyl or monocyclic aryl, preferably alkyl, and most preferably lower alkyl. Organometallic moieties are also useful nucleophilic groups for the purposes of the invention, particularly those that act as carbanion donors. Organometallic nucleophiles are not, however, preferred. Examples of organometallic moieties include: Grignard functionalitiesè $-R^6MgHal$ wherein $R^6$ is a carbon atom (substituted or unsubstituted), and Hal is halo, typically bromo, iodo or chloro, preferably bromo; and lithium-containing functionalities, typically alkyllithium groups; sodium-containing functionalities.

It will be appreciated by those of ordinary skill in the art that certain nucleophilic groups must be activated with a base so as to be capable of reaction with an electrophile. For example, when there are nucleophilic sulfhydryl and hydroxyl groups in the crosslinkable composition, the composition must be admixed with an aqueous base in order to remove a proton and provide an $-S^-$ or $-O^-$ species to enable reaction with an electrophile. Unless it is desirable for the base to participate in the crosslinking reaction, a non-nucleophilic base is preferred. In some embodiments, the base may be present as a component of a buffer solution. Suitable bases and corresponding crosslinking reactions are described infra in Section E.

The selection of electrophilic groups provided within the crosslinkable composition, i.e., on component B, must be made so that reaction is possible with the specific nucleophilic groups. Thus, when the X moieties are amino groups, the Y groups are selected so as to react with amino groups. Analogously, when the X moieties are sulfhydryl moieties, the corresponding electrophilic groups are sulfhydryl-reactive groups, and the like.

By way of example, when X is amino (generally although not necessarily primary amino), the electrophilic groups present on Y are amino reactive groups such as, but not limited to: (1) carboxylic acid esters, including cyclic esters and "activated" esters; (2) acid chloride groups ($-CO-Cl$); (3) anhydrides ($-(CO)-O-(CO)-R$); (4) ketones and aldehydes, including α,β-unsaturated aldehydes and ketones such as $-CH=CH-CH=O$ and $-CH=CH-C(CH_3)=O$; (5) halides; (6) isocyanate ($-N=C=O$); (7) isothiocyanate ($-N=C=S$); (8) epoxides; (9) activated hydroxyl groups (e.g., activated with conventional activating agents such as carbonyldiimidazole or sulfonyl chloride); and (10) olefins, including conjugate olefins, such as ethenesulfonyl ($-SO_2CH=CH_2$) and analogous functional groups, including acrylate ($-CO_2-C=CH_2$), methacrylate ($-CO_2-C(CH_3)=CH_2)$), ethyl acrylate ($-CO_2-C(CH_2CH_3)=CH_2$), and ethyleneimino ($-CH=CH-C=NH$). Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when X is sulfhydryl, the electrophilic groups present on Y are groups that react with a sulfhydryl moiety. Such reactive groups include those that form thioester linkages upon reaction with a sulfhydryl group, such as those described in applicants' PCT Publication No. WO 00/62827 to Wallace et al. As explained in detail therein, such "sulfhydryl reactive" groups include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive groups, auxiliary reagents can also be used to facilitate bond formation, e.g., 1-ethyl-3-[3-dimethylaminopropyl]carbodiimide can be used to facilitate coupling of sulfhydryl groups to carboxyl-containing groups.

In addition to the sulfhydryl reactive groups that form thioester linkages, various other sulfhydryl reactive functionalities can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups; such groups generally have the structure —S—S—Ar where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive groups forms thioether bonds with sulfhydryl groups. Such groups include, inter alia, maleimido, substituted maleimido, haloalkyl, epoxy, imino, and aziridino, as well as olefins (including conjugated olefins) such as ethenesulfonyl, etheneimino, acrylate, methacrylate, and α,β-unsaturated aldehydes and ketones. This class of sulfhydryl reactive groups is particularly preferred as the thioether bonds may provide faster crosslinking and longer in vivo stability.

When X is —OH, the electrophilic functional groups on the remaining component(s) must react with hydroxyl groups. The hydroxyl group may be activated as described above with respect to carboxylic acid groups, or it may react directly in the presence of base with a sufficiently reactive electrophile such as an epoxide group, an aziridine group, an acyl halide, or an anhydride.

When X is an organometallic nucleophile such as a Grignard functionality or an alkyllithium group, suitable electrophilic functional groups for reaction therewith are those containing carbonyl groups, including, by way of example, ketones and aldehydes.

It will also be appreciated that certain functional groups can react as nucleophiles or as electrophiles, depending on the selected reaction partner and/or the reaction conditions. For example, a carboxylic acid group can act as a nucleophile in the presence of a fairly strong base, but generally acts as an electrophile allowing nucleophilic attack at the carbonyl carbon and concomitant replacement of the hydroxyl group with the incoming nucleophile.

The covalent linkages in the crosslinked structure that result upon covalent binding of specific nucleophilic components to specific electrophilic components in the crosslinkable composition include, solely by way of example, the following (the optional linking groups $Q^1$ and $Q^2$ are omitted for clarity).

TABLE 1

| REPRESENTATIVE NUCLEOPHILIC COMPONENT (A, optional component C element $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CO)—O—N($COCH_2$) (succinimidyl carbonate terminus) | $R^1$—NH—(CO)—O—$R^2$ |
| $R^1$—SH | $R^2$—O—(CO)—O—N($COCH_2$) | $R^1$—S—(CO)—O—$R^2$ |
| $R^1$—OH | $R^2$—O—(CO)—O—N($COCH_2$) | $R^1$—O—(CO)—$R^2$ |
| $R^1$—$NH_2$ | $R^2$—O(CO)—CH=$CH_2$ (acrylate terminus) | $R^1$—NH—$CH_2CH_2$—(CO)—O—$R^2$ |
| $R^1$—SH | $R^2$—O—(CO)—CH=$CH_2$ | $R^1$—S—$CH_2CH_2$—(CO)—O—$R^2$ |
| $R^1$—OH | $R^2$—O—(CO)—CH=$CH_2$ | $R^1$—O—$CH_2CH_2$—(CO)—O—$R^2$ |
| $R^1$—$NH_2$ | $R^2$—O(CO)—$(CH_2)_3$—$CO_2$—N($COCH_2$) (succinimidyl glutarate terminus) | $R^1$—NH—(CO)—$(CH_2)_3$—(CO)—$OR^2$ |
| $R^1$—SH | $R^2$—O(CO)—$(CH_2)_3$—$CO_2$—N($COCH_2$) | $R^1$—S—(CO)—$(CH_2)_3$—(CO)—$OR^2$ |
| $R^1$—OH | $R^2$—O(CO)—$(CH_2)_3$—$CO_2$—N($COCH_2$) | $R^1$—O—(CO)—$(CH_2)_3$—(CO)—$OR^2$ |
| $R^1$—$NH_2$ | $R^2$—O—$CH_2$—$CO_2$—N($COCH_2$) (succinimidyl acetate terminus) | $R^1$—NH—(CO)—$CH_2$—$OR^2$ |
| $R^1$—SH | $R^2$—O—$CH_2$—$CO_2$—N($COCH_2$) | $R^1$—S—(CO)—$CH_2$—$OR^2$ |
| $R^1$—OH | $R^2$—O—$CH_2$—$CO_2$—N($COCH_2$) | $R^1$—O—(CO)—$CH_2$—$OR^2$ |
| $R^1$—$NH_2$ | $R^2$—O—NH(CO)—$(CH_2)_2$—$CO_2$—N($COCH_2$) (succinimidyl succinamide terminus) | $R^1$—NH—(CO)—$(CH_2)_2$—(CO)—NH—$OR^2$ |
| $R^1$—SH | $R^2$—O—NH(CO)—$(CH_2)_2$—$CO_2$—N($COCH_2$) | $R^1$—S—(CO)—$(CH_2)_2$—(CO)—NH—$OR^2$ |
| $R^1$—OH | $R^2$—O—NH(CO)—$(CH_2)_2$—$CO_2$—N($COCH_2$) | $R^1$—O—(CO)—$(CH_2)_2$—(CO)—NH—$OR^2$ |
| $R^1$—$NH_2$ | $R^2$—O—$(CH_2)_2$—CHO (propionaldehyde terminus) | $R^1$—NH—(CO)—$(CH_2)_2$—$OR^2$ |

TABLE 1-continued

| REPRESENTATIVE NUCLEOPHILIC COMPONENT (A, optional component C element $FN_{NU}$) | REPRESENTATIVE ELECTROPHILIC COMPONENT (B, $FN_{EL}$) | RESULTING LINKAGE |
|---|---|---|
| $R^1—NH_2$ | 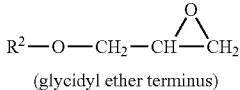<br>(glycidyl ether terminus) | $R^1—NH—CH_2—CH(OH)—CH_2—OR^2$<br>and<br>$R^1—N[CH_2—CH(OH)—CH_2—OR^2]_2$ |
| $R^1—NH_2$ | $R^2—SO_2—CH=CH_2$<br>(vinyl sulfone terminus) | $R^1—NH—CH_2CH_2—SO_2—R^2$ |
| $R^1—SH$ | $R^2—SO_2—CH=CH_2$ | $R^1—S—CH_2CH_2—SO_2—R^2$ |

Linking Groups

The functional groups X and Y and FN on optional component C may be directly attached to the compound core ($R^1$, $R^2$ or $R^3$ on optional component C, respectively), or they may be indirectly attached through a linking group, with longer linking groups also termed "chain extenders." In structural formulae (I), (II) and (III), the optional linking groups are represented by $Q^1$, $Q^2$, and $Q^3$, wherein the linking groups are present when q, r and s are equal to 1 (with R, X, Y, Fn, m, n and p as defined previously).

Suitable linking groups are well known in the art. See, for example, International Patent Publication No. WO 97/22371. Linking groups are useful to avoid steric hindrance problems that are sometimes associated with the formation of direct linkages between molecules. Linking groups may additionally be used to link several multifunctionally activated compounds together to make larger molecules. In a preferred embodiment, a linking group can be used to alter the degradative properties of the compositions after administration and resultant gel formation. For example, linking groups can be incorporated into components A, B, or optional component C to promote hydrolysis, to discourage hydrolysis, or to provide a site for enzymatic degradation.

Examples of linking groups that provide hydrolyzable sites, include, inter alia: ester linkages; anhydride linkages, such as obtained by incorporation of glutarate and succinate; ortho ester linkages; ortho carbonate linkages such as trimethylene carbonate; amide linkages; phosphoester linkages; α-hydroxy acid linkages, such as may be obtained by incorporation of lactic acid and glycolic acid; lactone-based linkages, such as may be obtained by incorporation of caprolactone, valerolactone, γ-butyrolactone and p-dioxanone; and amide linkages such as in a dimeric, oligomeric, or poly (amino acid) segment. Examples of non-degradable linking groups include succinimide, propionic acid, and carboxymethylate linkages. See, for example, PCT WO 99/07417. Examples of enzymatically degradable linkages include Leu-Gly-Pro-Ala, which is degraded by collagenase; and Gly-Pro-Lys, which is degraded by plasmin.

Linking groups can also enhance or suppress the reactivity of the various nucleophilic and electrophilic groups. For example, electron-withdrawing groups within one or two carbons of a sulfhydryl group would be expected to diminish its effectiveness in coupling, due to a lowering of nucleophilicity. Carbon-carbon double bonds and carbonyl groups will also have such an effect. Conversely, electron-withdrawing groups adjacent to a carbonyl group (e.g., the reactive carbonyl of glutaryl-N-hydroxysuccinimidyl) would increase the reactivity of the carbonyl carbon with respect to an incoming nucleophile. By contrast, sterically bulky groups in the vicinity of a functional group can be used to diminish reactivity and thus coupling rate as a result of steric hindrance.

By way of example, particular linking groups and corresponding component structure are indicated in Table 2.

TABLE 2

| LINKING GROUP | COMPONENT STRUCTURE |
|---|---|
| $—O—(CH_2)_n—$ | Component A: $R^1—O—(CH_2)_n—X$<br>Component B: $R^2—O—(CH_2)_n—Y$<br>Optional Component C: $R^3—O—(CH_2)_n-Z$ |
| $—S—(CH_2)_n—$ | Component A: $R^1—S—(CH_2)_n—X$<br>Component B: $R^2—S—(CH_2)_n—Y$<br>Optional Component C: $R^3—S—(CH_2)_n-Z$ |
| $—NH—(CH_2)_n—$ | Component A: $R^1—NH—(CH_2)_n—X$<br>Component B: $R^2—NH—(CH_2)_n—Y$<br>Optional Component C: $R^3—NH—(CH_2)_n-Z$ |
| $—O—(CO)—NH—(CH_2)_n—$ | Component A: $R^1—O—(CO)—NH—(CH_2)_n—X$<br>Component B: $R^2—O—(CO)—NH—(CH_2)_n—Y$<br>Optional Component C: $R^3—O—(CO)—NH—(CH_2)_n-Z$ |
| $—NH—(CO)—O—(CH_2)_n—$ | Component A: $R^1—NH—(CO)—O—(CH_2)_n—X$<br>Component B: $R^2—NH—(CO)—O—(CH_2)_n—Y$<br>Optional Component C: $R^3—NH—(CO)—O—(CH_2)_n-Z$ |
| $—O—(CO)—(CH_2)_n—$ | Component A: $R^1—O—(CO)—(CH_2)_n—X$<br>Component B: $R^2—O—(CO)—(CH_2)_n—Y$<br>Optional Component C: $R^3—O—(CO)—(CH_2)_n-Z$ |
| $—(CO)—O—(CH_2)_n—$ | Component A: $R^1—(CO)—O—(CH_2)_n—X$<br>Component B: $R^2—(CO)—O—(CH_2)_n—Y$<br>Optional Component C: $R^3—(CO)—O—(CH_2)_n-Z$ |

TABLE 2-continued

| LINKING GROUP | COMPONENT STRUCTURE |
|---|---|
| —O—(CO)—O—(CH$_2$)$_n$— | Component A: R$^1$—O—(CO)—O—(CH$_2$)$_n$—X |
| | Component B: R$^2$—O—(CO)—O—(CH$_2$)$_n$—Y |
| | Optional Component C: R$^3$—O—(CO)—O—(CH$_2$)$_n$-Z |
| —O—(CO)—CHR$^7$— | Component A: R$^1$—O—(CO)—CHR$^7$—X |
| | Component B: R$^2$—O—(CO)—CHR$^7$—Y |
| | Optional Component C: R$^3$—O—(CO)—CHR$^7$-Z |
| —O—R$^8$—(CO)—NH— | Component A: R$^1$—O—R$^8$—(CO)—NH—X |
| | Component B: R$^2$—O—R$^8$—(CO)—NH—Y |
| | Optional Component C: R$^3$—O—R$^8$—(CO)—NH-Z |

In the table, n is generally in the range of 1 to about 10, R$^7$ is generally hydrocarbyl, typically alkyl or aryl, preferably alkyl, and most preferably lower alkyl, and R$^8$ is hydrocarbylene, heteroatom-containing hydrocarbylene, substituted hydrocarbylene, or substituted heteroatom-containing hydrocarbylene) typically alkylene or arylene (again, optionally substituted and/or containing a heteroatom), preferably lower alkylene (e.g., methylene, ethylene, n-propylene, n-butylene, etc.), phenylene, or amidoalkylene (e.g., —(CO)—NH—CH$_2$).

Other general principles that should be considered with respect to linking groups are as follows: If higher molecular weight components are to be used, they preferably have biodegradable linkages as described above, so that fragments larger than 20,000 mol. wt. are not generated during resorption in the body. In addition, to promote water miscibility and/or solubility, it may be desired to add sufficient electric charge or hydrophilicity. Hydrophilic groups can be easily introduced using known chemical synthesis, so long as they do not give rise to unwanted swelling or an undesirable decrease in compressive strength. In particular, polyalkoxy segments may weaken gel strength.

The Component Core

The "core" of each crosslinkable component is comprised of the molecular structure to which the nucleophilic or electrophilic groups are bound. Using the formulae (I) R$^1$-[Q$^1$]$_q$-X)$_m$, for component A, (II) R$^2$(-[Q$^2$]$_r$-Y)$_n$ for component B, and (III) R$^3$(-[Q$^3$]$_s$-Fn)$_p$ for optional component C, the "core" groups are R$^1$, R$^2$ and R$^3$. Each molecular core of the reactive components of the crosslinkable composition is generally selected from synthetic and naturally occurring hydrophilic polymers, hydrophobic polymers, and C$_2$-C$_{14}$ hydrocarbyl groups zero to 2 heteroatoms selected from N, O and S, with the proviso that at least one of the crosslinkable components A, B, and optionally C, comprises a molecular core of a synthetic hydrophilic polymer. In a preferred embodiment, at least one of A and B comprises a molecular core of a synthetic hydrophilic polymer.

Hydrophilic Polymers and "Activation" Thereof

A "hydrophilic polymer" as used herein refers to a synthetic polymer having an average molecular weight and composition effective to render the polymer "hydrophilic" as defined in Part (I) of this section. As discussed above, synthetic hydrophilic polymers useful herein include, but are not limited to: polyalkylene oxides, particularly polyethylene glycol and poly(ethylene oxide)-polypropylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethyl-methacrylate), poly (hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly (N-vinyl caprolactam), and copolymers thereof; polyoxazolines, including poly(methyloxazoline) and poly(ethyloxazoline); and polyvinylamines. It must be emphasized that the aforementioned list of polymers is not exhaustive, and a variety of other synthetic hydrophilic polymers may be used, as will be appreciated by those skilled in the art.

The synthetic hydrophilic polymer may be a homopolymer, a block copolymer, a random copolymer, or a graft copolymer. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly (orthocarbonate) segments, and the like.

Other suitable synthetic hydrophilic polymers include chemically synthesized polypeptides, particularly polynucleophilic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000. Poly(lysine)s for use in the present invention preferably have a molecular weight within the range of about 1,000 to about 300,000, more preferably within the range of about 5,000 to about 100,000, and most preferably, within the range of about 8,000 to about 15,000. Poly(lysine)s of varying molecular weights are commercially available from Peninsula Laboratories, Inc. (Belmont, Calif.).

The synthetic hydrophilic polymer may be a homopolymer, a block copolymer, a random copolymer, or a graft copolymer. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly (orthocarbonate) segments, and the like.

Although a variety of different synthetic hydrophilic polymers can be used in the present compositions, as indicated above, preferred synthetic hydrophilic polymers are polyethylene glycol (PEG) and polyglycerol (PG), particularly highly branched polyglycerol. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred synthetic hydrophilic polymer for certain applications is a polyethylene glycol (PEG) having a molecular weight within the range of about 100 to about 100,000 mol. wt., although for highly branched PEG, far higher molecular weight polymers can be employed, e.g., up to 1,000,000 or more, providing that biodegradable sites are incorporated ensuring that all degradation products will have a molecular weight of less than about 30,000. For most PEGs, however, the preferred molecular weight is about 1,000 to about 20,000 mol. wt., more preferably within the range of about 7,500 to about 20,000 mol. wt. Most preferably, the polyethylene glycol has a molecular weight of approximately 10,000 mol. wt.

Naturally occurring hydrophilic polymers include, but are not limited to: proteins such as collagen, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen and glycosaminoglycans are preferred naturally occurring hydrophilic polymers for use herein.

Any of the hydrophilic polymers herein must contain, or be activated to contain, functional groups, i.e., nucleophilic or electrophilic groups, which enable crosslinking Activation of PEG is discussed below; it is to be understood, however, that the following discussion is for purposes of illustration and analogous techniques may be employed with other polymers.

With respect to PEG, first of all, various functionalized polyethylene glycols have been used effectively in fields such as protein modification (see Abuchowski et al., *Enzymes as Drugs*, John Wiley & Sons: New York, N.Y., pp. 367-383 (1981); and Dreborg et al., *Crit. Rev. Therap. Drug Carrier Syst.* 6:315 (1990)), peptide chemistry (see Mutter et al., *The Peptides*, Academic: New York, N.Y. 2:285-332 [DATE?]; and Zalipsky et al., *Int. J. Peptide Protein Res.* 30:740 (1987)), and the synthesis of polymeric drugs (see Zalipsky et al., *Eur. Polym. J.* 19:1177 (1983); and Ouchi et al., *J. Macromol. Sci. Chem. A*24:1011 (1987)).

Activated forms of PEG, including multifunctionally activated PEG, are commercially available, and are also easily prepared using known methods. For example, see Chapter 22 of *Poly(ethylene Glycol) Chemistry: Biotechnical and Biomedical Applications*, J. Milton Harris, ed., Plenum Press, NY (1992); and Shearwater Polymers, Inc. Catalog, Polyethylene Glycol Derivatives, Huntsville, Ala. (1997-1998).

Structures for some specific, tetrafunctionally activated forms of PEG are shown in FIGS. 1 to 10, as are generalized reaction products obtained by reacting the activated PEGs with multi-amino PEGs, i.e., a PEG with two or more primary amino groups. The activated PEGs illustrated have a pentaerythritol (2,2-bis(hydroxymethyl)-1,3-propanediol) core. Such activated PEGs, as will be appreciated by those in the art, are readily prepared by conversion of the exposed hydroxyl groups in the PEGylated polyol (i.e., the terminal hydroxyl groups on the PEG chains) to carboxylic acid groups (typically by reaction with an anhydride in the presence of a nitrogenous base), followed by esterification with N-hydroxysuccinimide, N-hydroxysulfosuccinimide, or the like, to give the polyfunctionally activated PEG.

FIG. 1 shows the reaction of tetrafunctionally activated PEG succinimidyl glutarate, referred to herein as "SG-PEG," with multi-amino PEG, and the reaction product obtained thereby.

Figure 2:
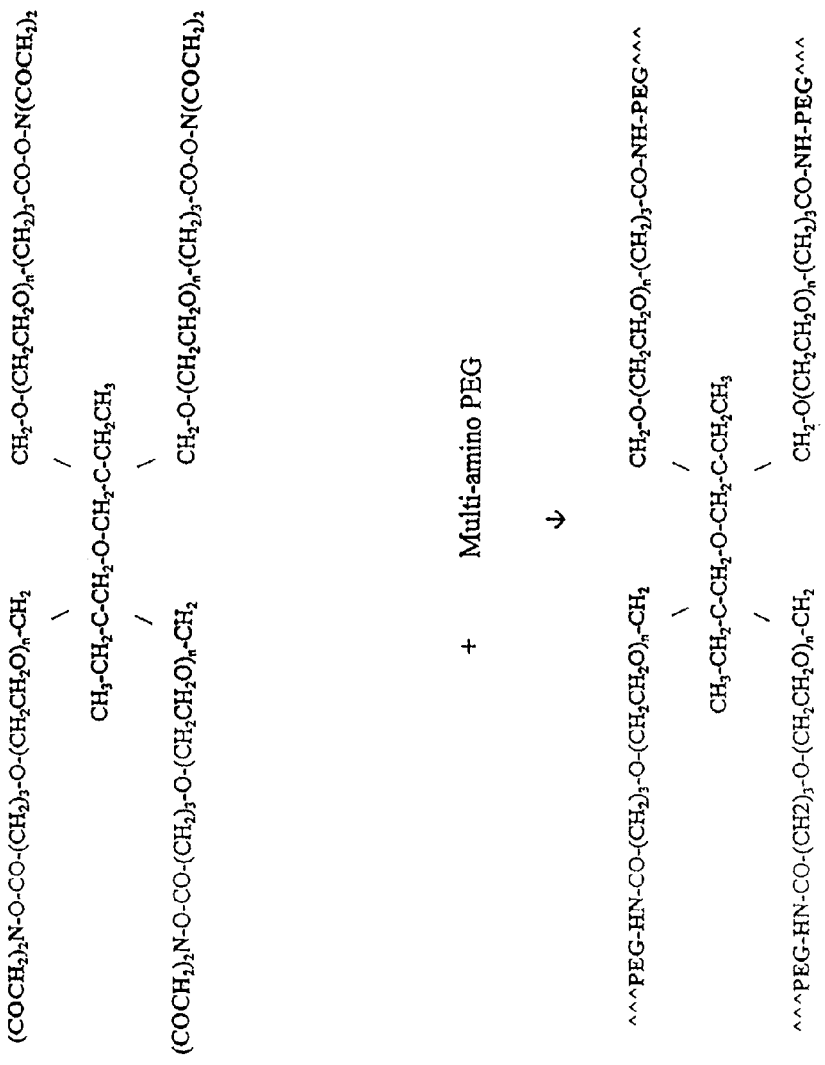

Another activated form of PEG is PEG succinimidyl propionate ("SE-PEG"). The structural formula for tetrafunctionally activated SE-PEG and the reaction product obtained upon reaction with multi-amino PEG are shown in FIG. 2.

Figure 3:
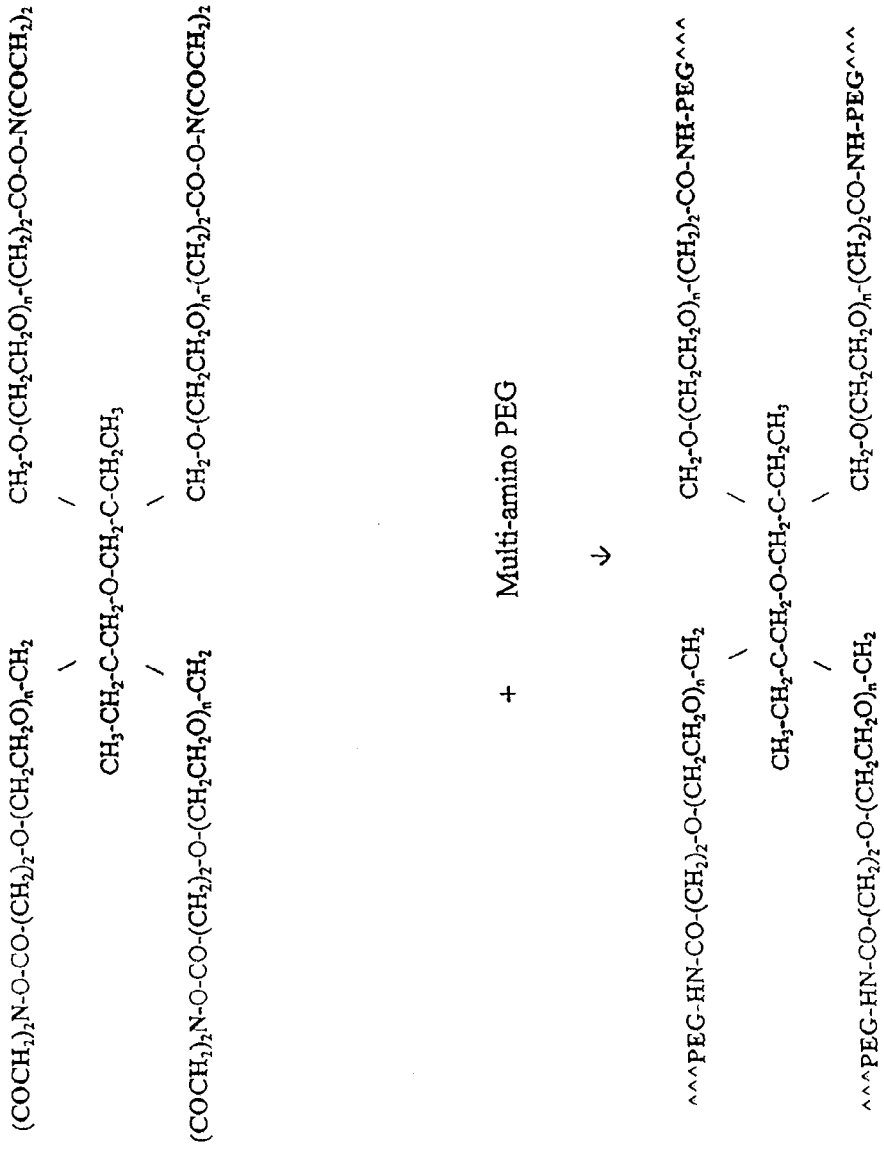
Figure 4:
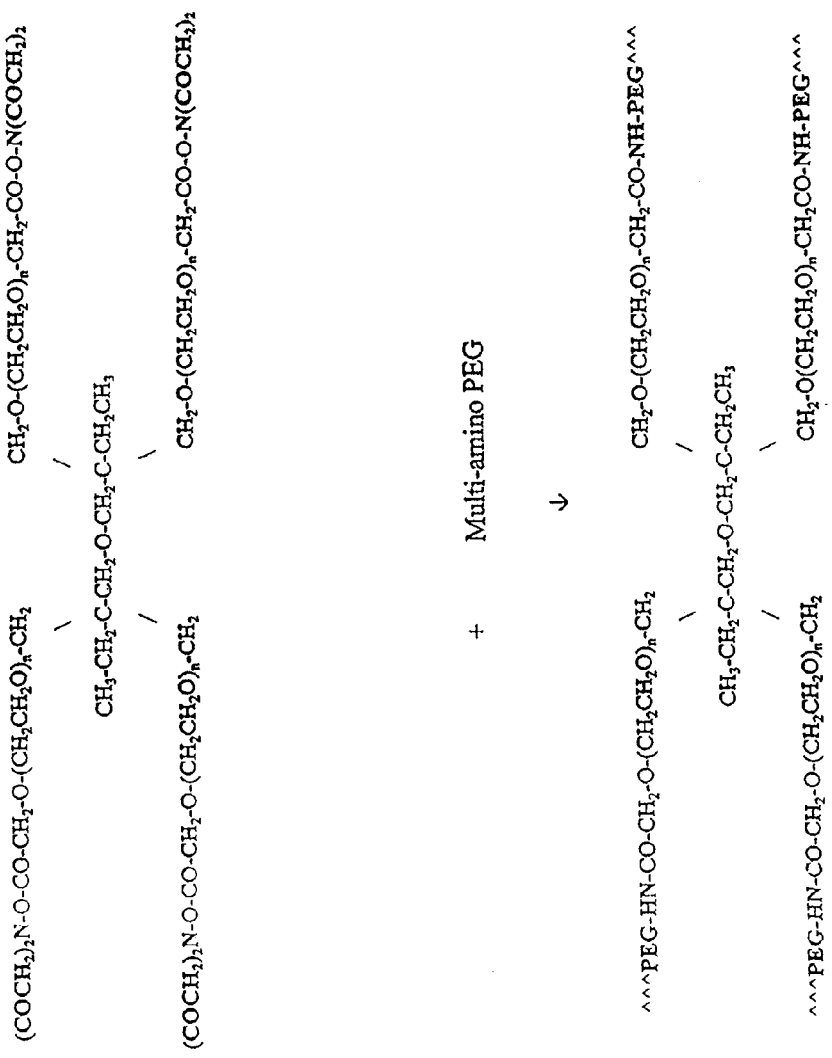

Analogous activated forms of PEG are PEG succinimidyl butylate and PEG succinimidyl acetate, the structures of which are shown in FIGS. 3 and 4, respectively, along with the reaction products obtained upon reaction with multi-amino PEG. SE-PEG, PEG succinimidyl butylate, and PEG succinimidyl acetate are sometimes referred to as "PEG succinimidyl" (PEG-S); see U.S. Pat. No. 5,328,955 to Rhee et al.

Figure 5:
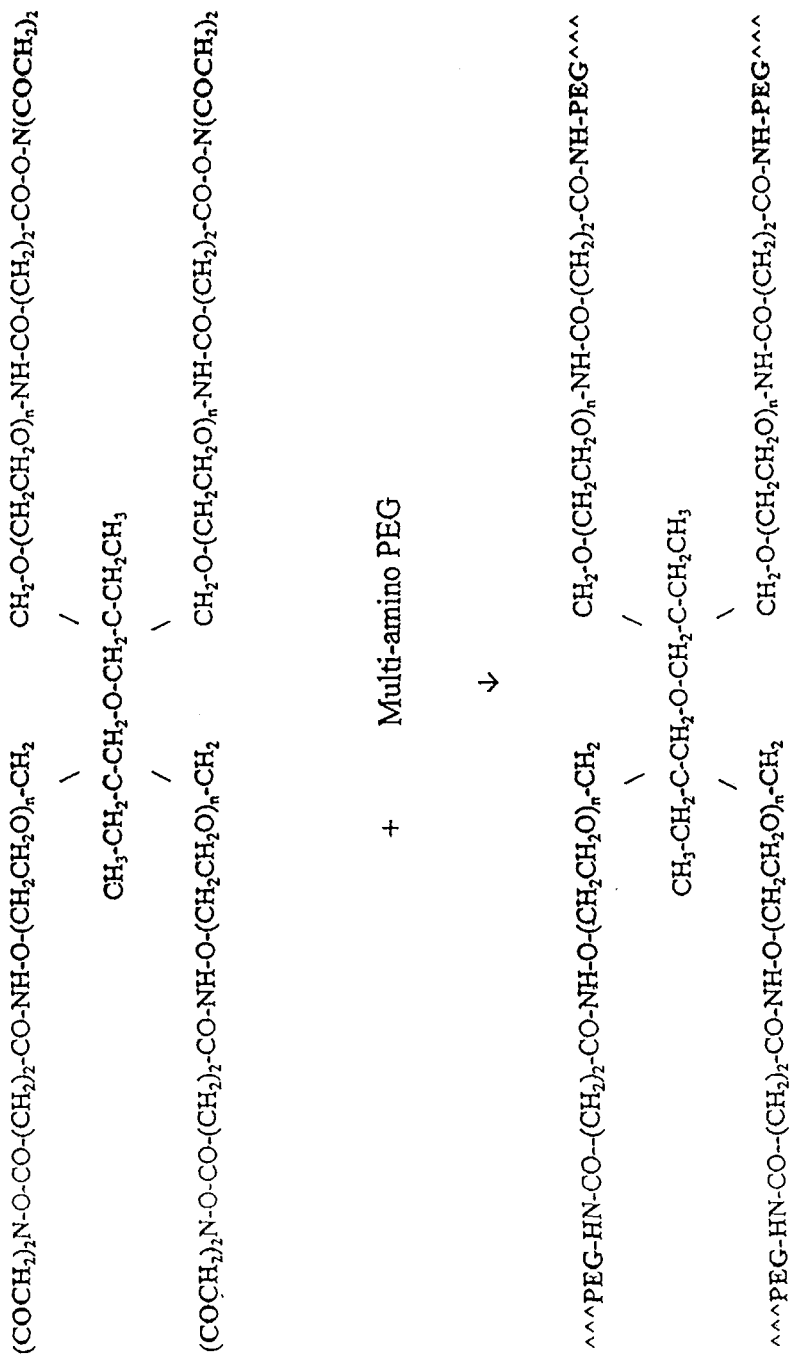

Another functionally activated form of PEG is referred to as "PEG succinimidyl succinamide" (SSA-PEG). The structural formula for the tetrafunctionally activated form of this compound and the reaction product obtained by reacting it with multi-amino PEG are shown in FIG. 5. In the structure of FIG. 5, an ethylene (—$CH_2CH_2$—) group is shown adjacent to the succinimidyl ester; it is to be understood, however, that as with the PEG succinimidyl compounds, related structures containing a methylene linkage, an n-propylene linkage, or the like, are also possible.

Figure 6:
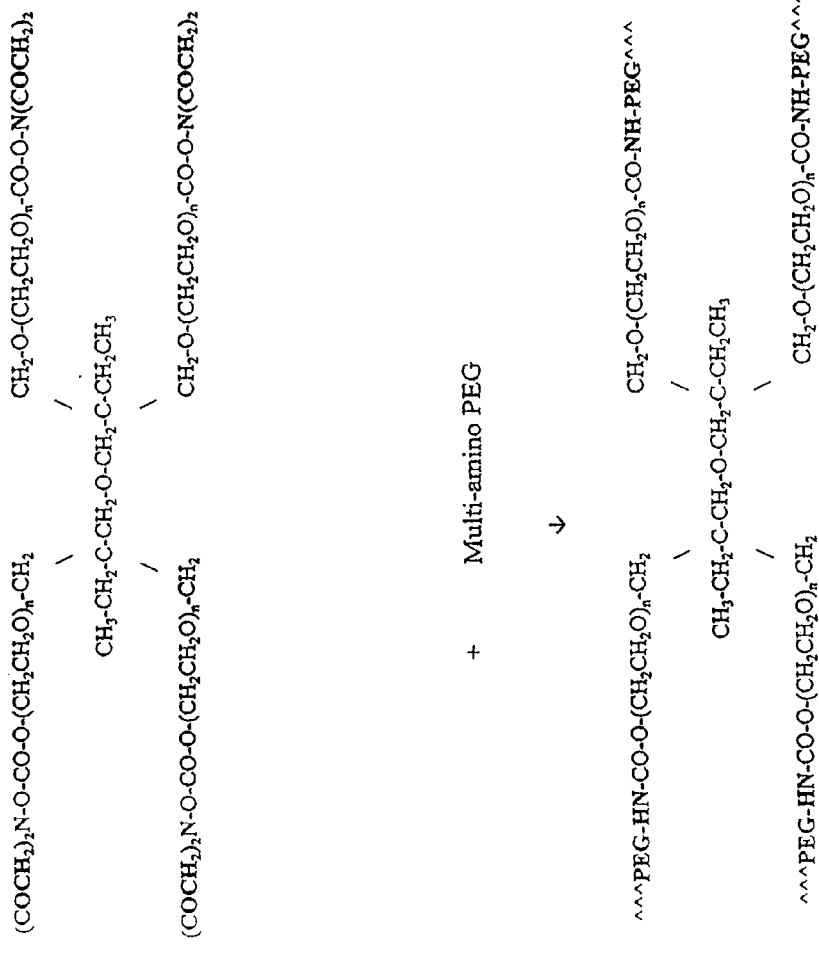

Yet another activated form of PEG is PEG succinimidyl carbonate (SC-PEG). The structural formula of tetrafunctionally activated SC-PEG and the conjugate formed by reacting it with multi-amino PEG are shown in FIG. 6.

Figure 7:
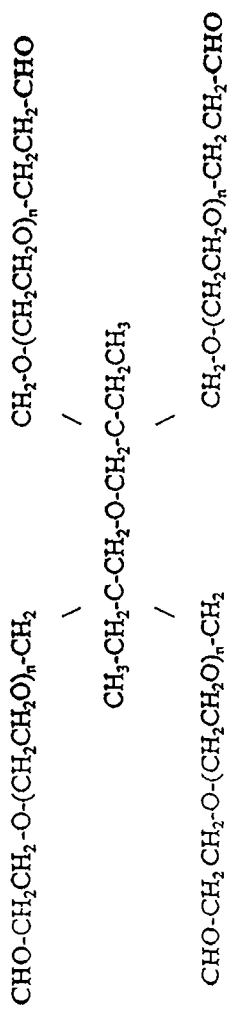
Figure 7:
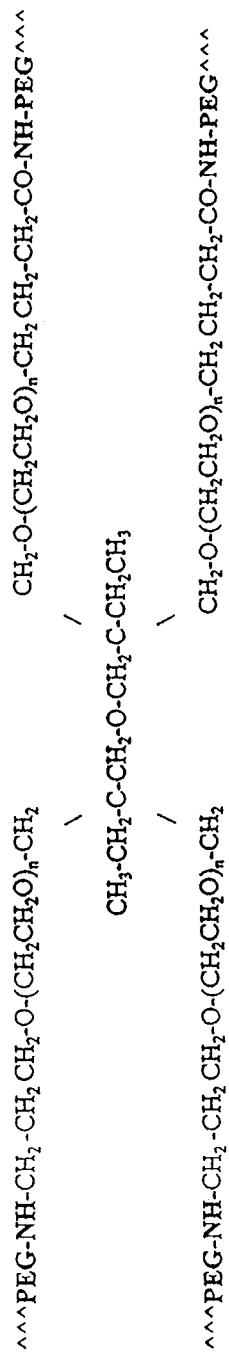

PEG can also be derivatized to form functionally activated PEG propionaldehyde (A-PEG), the tetrafunctionally activated form of which is shown in FIG. 7, as is the conjugate formed by the reaction of A-PEG with multi-amino PEG.

Figure 8:
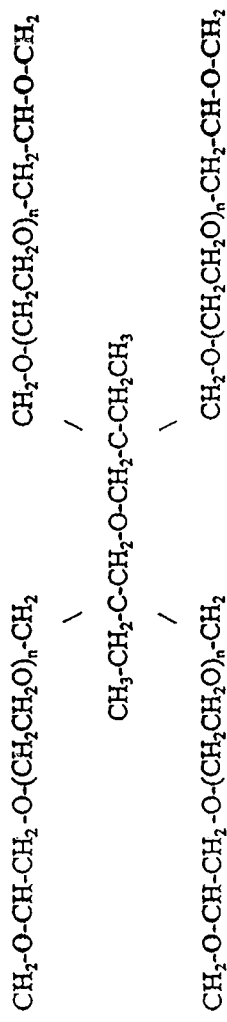
Figure 8:
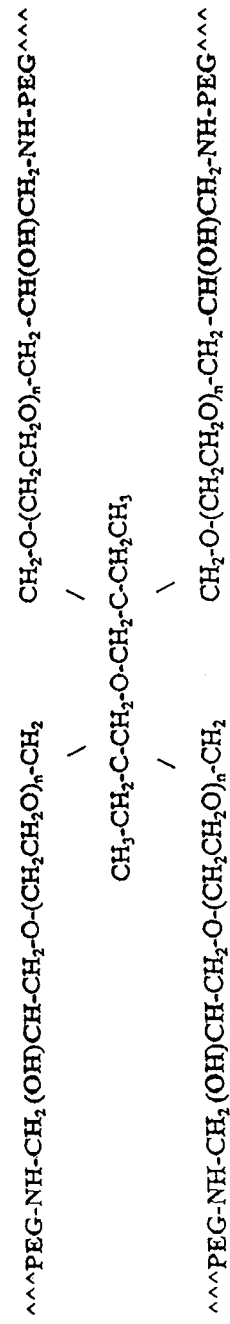

Yet another form of activated polyethylene glycol is functionally activated PEG glycidyl ether (E-PEG), of which the tetrafunctionally-activated compound is shown in FIG. 8, as is the conjugate formed by reacting such with multi-amino PEG.

Figure 9:
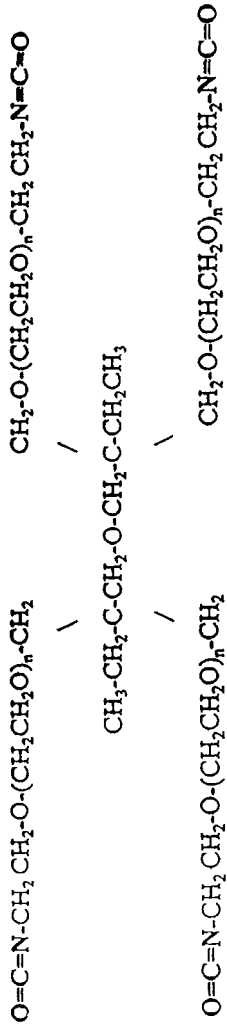
Figure 9:
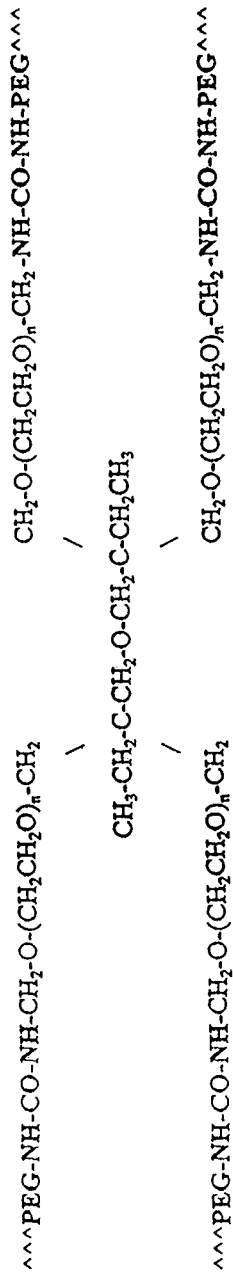

Another activated derivative of polyethylene glycol is functionally activated PEG-isocyanate (1-PEG), which is shown in FIG. 9, along with the conjugate formed by reacting such with multi-amino PEG.

Figure 10:
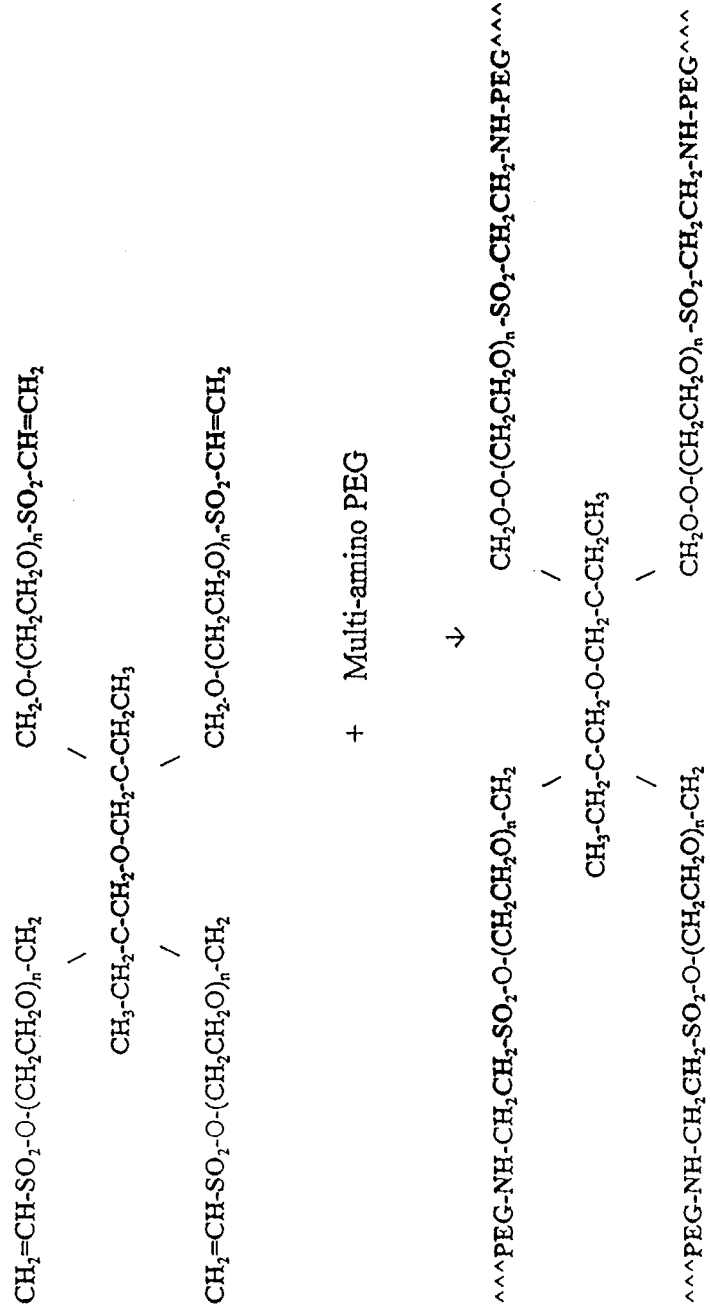

Another activated derivative of polyethylene glycol is functionally activated PEG-vinylsulfone (V-PEG), which is shown in FIG. 10, along with the conjugate formed by reacting such with multi-amino PEG.

Activation with succinimidyl groups to convert terminal carboxylic acid groups to reactive esters is one technique for preparing a synthetic hydrophilic polymer with electrophilic moieties suitable for reaction with nucleophiles such as primary amines, thiols, and hydroxyl groups. Other activating agents for hydroxyl groups include carbonyldiimidazole and sulfonyl chloride. However, as discussed in part (B) of this section, a wide variety of electrophilic groups may be advantageously employed for reaction with corresponding nucleophiles. Examples of such electrophilic groups include acid chloride groups; anhydrides, ketones, aldehydes, isocyanate, isothiocyanate, epoxides, and olefins, including conjugated olefins such as ethenesulfonyl($-SO_2CH=CH_2$) and analogous functional groups.

Hydrophilic di- or poly-nucleophilic polymers of the present composition are exemplified in FIGS. 1-10 by multi-amino PEG. Various forms of multi-amino PEG are commercially available from Shearwater Polymers (Huntsville, Ala.) and from Texaco Chemical Company (Houston, Tex.) under the name "Jeffamine". Multi-amino PEGs useful in the present invention include Texaco's Jeffamine diamines ("D" series) and triamines ("T" series), which contain two and three primary amino groups per molecule. Analogous poly (sulfhydryl) PEGs are also available from Shearwater Polymers, e.g., in the form of pentaerythritol poly(ethylene glycol) ether tetra-sulfhydryl (molecular weight 10,000).

Hydrophobic Polymers

The crosslinkable compositions of the invention can also include hydrophobic polymers, although for most uses hydrophilic polymers are preferred. Polylactic acid and polyglycolic acid are examples of two hydrophobic polymers that can be used. With other hydrophobic polymers, only short-chain oligomers should be used, containing at most about 14 carbon atoms, to avoid solubility-related problems during reaction.

Low Molecular Weight Components

As indicated above, the molecular core of one or more of the crosslinkable components can also be a low molecular weight compound, i.e., a $C_2$-$C_{14}$ hydrocarbyl group containing zero to 2 heteroatoms selected from N, O, S and combinations thereof. Such a molecular core can be substituted with nucleophilic groups or with electrophilic groups.

When the low molecular weight molecular core is substituted with primary amino groups, the component may be, for example, ethylenediamine ($H_2N-CH_2CH_2-NH_2$), tetramethylenediamine ($H_2N_4-CH_4)-NH_2$), pentamethylenediamine (cadaverine) ($H_2N-(CH_5)-NH_2$), hexamethylenediamine ($H_2N_4-CH_6)-NH_2$), bis(2-aminoethyl)amine (HN$-[CH_2CH_2-NH_2]_2$), or tris(2-aminoethyl)amine (N$-[CH_2CH_2-NH_2]_3$).

Low molecular weight diols and polyols include trimethylolpropane, di(trimethylol propane), pentaerythritol, and diglycerol, all of which require activation with a base in order to facilitate their reaction as nucleophiles. Such diols and polyols may also be functionalized to provide di- and poly-carboxylic acids, functional groups that are, as noted earlier herein, also useful as nucleophiles under certain conditions. Polyacids for use in the present compositions include, without limitation, trimethylolpropane-based tricarboxylic acid, di(trimethylol propane)-based tetracarboxylic acid, heptanedioic acid, octanedioic acid (suberic acid), and hexadecanedioic acid (thapsic acid), all of which are commercially available or readily synthesized using known techniques.

Low molecular weight di- and poly-electrophiles include, for example, disuccinimidyl suberate (DSS), bis(sulfosuccinimidyl) suberate ($BS_3$), dithiobis(succinimidylpropionate) (DSP), bis(2-succinimidooxycarbonyloxy)ethyl sulfone (BSOCOES), and 3,3'-dithiobis(sulfosuccinimidylpropionate (DTSPP), and their analogs and derivatives. The aforementioned compounds are commercially available from Pierce (Rockford, Ill.). Such di- and poly-electrophiles can also be synthesized from di- and polyacids, for example by reaction with an appropriate molar amount of N-hydroxysuccinimide in the presence of DCC. Polyols such as trimethylolpropane and di(trimethylol propane) can be converted to carboxylic acid form using various known techniques, then further derivatized by reaction with NHS in the presence of DCC to produce trifunctionally and tetrafunctionally activated polymers.

Storage and Handling

Because crosslinkable components containing electrophilic groups react with water, the electrophilic component or components are generally stored and used in sterile, dry form to prevent hydrolysis. Processes for preparing synthetic hydrophilic polymers containing multiple electrophilic groups in sterile, dry form are set forth in commonly assigned U.S. Pat. No. 5,643,464 to Rhee et al. For example, the dry synthetic polymer may be compression molded into a thin sheet or membrane, which can then be sterilized using gamma or, preferably, e-beam irradiation. The resulting dry membrane or sheet can be cut to the desired size or chopped into smaller size particulates.

Components containing multiple nucleophilic groups are generally not water-reactive and can therefore be stored either dry or in aqueous solution. If stored as a dry, particulate, solid, the various components of the crosslinkable composition may be blended and stored in a single container. Admixture of all components with water, saline, or other aqueous media should not occur until immediately prior to use.

In an alternative embodiment, the crosslinking components can be mixed together in a single aqueous medium in which they are both unreactive, i.e. such as in a low pH buffer. Thereafter, they can be sprayed onto the targeted tissue site along with a high pH buffer, after which they will rapidly react and form a gel.

Suitable liquid media for storage of crosslinkable compositions include aqueous buffer solutions such as monobasic sodium phosphate/dibasic sodium phosphate, sodium carbonate/sodium bicarbonate, glutamate or acetate, at a concentration of 0.5 to 300 mM. In general, a sulfhydryl-reactive component, such as PEG substituted with maleimido groups or succinimidyl esters, is prepared in water or a dilute buffer, with a pH of between around 5 to 6. Buffers with pKs between about 8 and 10.5 for preparing a polysulfhydryl component such as sulfhydryl-PEG are useful to achieve fast gelation time of compositions containing mixtures of sulfhydryl-PEG and SG-PEG. These include carbonate, borate and AMPSO (3-[(1,1-dimethyl-2-hydroxyethyl)amino]2-hydroxy-propane-sulfonic acid). In contrast, using a combination of maleimidyl PEG and sulfhydryl-PEG, a pH of around 5 to 9 is preferred for the liquid medium used to prepare the sulfhydryl PEG.

Other Components

In order to enhance adhesive strength, it may be generally desirable to add a "tensile strength enhancer" to the adhesive composition. Such tensile strength enhancers preferably comprise micron-size, preferably 5 to 40 microns in diameter and 20 to 5000 microns in length, high tensile strength fibers, usually with glass transition temperatures well above 37° C.

Suitable tensile strength enhancers for use in the present invention include, inter alia, collagen fibers, polyglycolide and polylactide fibers, as well as other organic tensile strength enhancers and inorganic tensile strength enhancers. A particularly useful tensile strength enhancer is VICRYL® (polyglycolide:polylactide, 90:10). Suitable tensile strength enhancers are those that have inherent high tensile strength and also can interact by covalent or non-covalent bonds with the polymerized gel network. The tensile strength enhancer should bond to the gel, either mechanically or covalently, in order to provide tensile support. Tensile strengths of polyglycolide resorbable sutures are approximately 89,000 N/cm$^2$; that of collagen fibers is 5000-10,000 N/cm$^2$ (Hayashi, T., in Biomedical Applic. of Polym. Mater., Tsuruta, T. et al., Eds., CRC Press, Boca Raton, Fla., 1993).

The adhesive composition of the invention may also be used for localized delivery of various drugs and other biologically active agents in conjunction with the repair of herniated tissue. Biologically active agents such as growth factors may be delivered from the composition to a local tissue site in order to facilitate tissue healing and regeneration.

The term "biologically active agent" refers to an organic molecule that exerts biological effects in vivo. Examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and genes that can be incorporated into the compositions of the invention.

Preferred biologically active agents for use in the compositions of the present invention are cytokines, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the TGF supergene family include the beta transforming growth factors (for example, TGF-$\beta_1$, TGF-$\beta_2$, TGF-$\beta_3$); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Biologically active agents may be incorporated into the adhesive composition by admixture. Alternatively, the agents may be incorporated into the crosslinked polymer matrix by binding these agents to the functional groups on the synthetic polymers. Processes for covalently binding biologically active agents such as growth factors using functionally activated polyethylene glycols are described in commonly assigned U.S. Pat. No. 5,162,430, issued Nov. 10, 1992, to Rhee et al. Such compositions preferably include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the crosslinked polymer composition involves mixing the active agent with a polyelectrophilic component prior to addition of the polynucleophilic component.

By varying the relative molar amounts of the different components of the crosslinkable composition, it is possible to alter the net charge of the resulting crosslinked polymer composition, in order to prepare a matrix for the delivery of a charged compound such as a protein or ionizable drug. As such, the delivery of charged proteins or drugs, which would normally diffuse rapidly out of a neutral carrier matrix, can be controlled.

For example, if a molar excess of a polynucleophilic component is used, the resulting matrix has a net positive charge and can be used to ionically bind and deliver negatively charged compounds. Examples of negatively charged compounds that can be delivered from these matrices include various drugs, cells, proteins, and polysaccharides. Negatively charged collagens, such as succinylated collagen, and glycosaminoglycan derivatives such as sodium hyaluronate, keratan sulfate, keratosulfate, sodium chondroitin sulfate A, sodium dermatan sulfate B, sodium chondroitin sulfate C, heparin, esterified chondroitin sulfate C, and esterified heparin, can be effectively incorporated into the crosslinked polymer matrix as described above.

If a molar excess of a polyelectrophilic component is used, the resulting matrix has a net negative charge and can be used to ionically bind and deliver positively charged compounds. Examples of positively charged compounds that can be delivered from these matrices include various drugs, cells, proteins, and polysaccharides. Positively charged collagens, such as methylated collagen, and glycosaminoglycan derivatives such as esterified deacetylated hyaluronic acid, esterified deacetylated desulfated chondroitin sulfate A, esterified deacetylated desulfated chondroitin sulfate C, deacetylated desulfated keratan sulfate, deacetylated desulfated keratosulfate, esterified desulfated heparin, and chitosan, can be effectively incorporated into the crosslinked polymer matrix as described above.

The adhesive compositions can also be prepared to contain various colorants or imaging agents such as synthetic dyes and natural coloring agents, light-emissive and fluorescent dyes, iodine or barium sulfate, or fluorine, in order to aid visualization of the compositions after administration via optical, X-ray or $^{19}$F-MRI detection means. Suitable colorants include, but are not limited to, FD&C dyes and FD&C lakes, (e.g., allura red AC, amaranth, brilliant blue FCF, quinoline yellow, sunset yellow FCF), black PN, Bordeaux B, Brown FK, Brown HT, canthaxanthin, carmine, carmoisine, beetroot red, chlorophyll, conchineal, curcumin, eosin, erythrosine, green S, ponceau 4R, red 2G, saffron, tartrazine, turmeric, and mixtures thereof. Examples of light-emissive and fluorescent dyes include: fluorescein, rose bengal, indocyanine green, analogue members of the tricarbocyanine dyes; and many others. In selecting a suitable dye, color and luminescent efficiency are two important factors. Luminescent dyes found particularly suitable include cyanine and related polymethine dyes, merocyanine, styryl and oxonol dyes. Other suitable coloring agents, light-emissive dyes, and fluorescent dyes will be obvious to those skilled in the art. It may also be desirable to incorporate proteins such as albumin, fibrin, or fibrinogen into the crosslinked polymer composition to promote cellular adhesion. In addition, the introduction of hydrocolloids such as carboxymethylcellulose may promote tissue adhesion.

Crosslinking of the Adhesive Composition

Any number of crosslinking techniques may be used to effect crosslinking of the aforementioned compositions. Generally, however, components A, B, and optionally C are selected such that crosslinking occurs fairly rapidly upon admixture of all components of the crosslinkable composition with an aqueous medium.

For crosslinking compositions in which one or more components contain hydroxyl and/or thiol groups as nucleophilic moieties, the aqueous medium with which the crosslinking composition (or components thereof) are admixed should contain a basic reagent that is effective to increase the nucleophilic reactivity of the hydroxyl and/or thiol group (and thus the rate of the nucleophile-electrophile reactions) but that is preferably non-nucleophilic so as to avoid reaction with any electrophilic groups present. A catalytic amount of base can be used, and/or a base-containing buffer. In an alternative but less preferred embodiment, a reactive base can be used that participates as a reactant in the crosslinking reaction.

In general, the combined concentration of all crosslinkable components in the aqueous admixture will be in the range of about 1 to 50 wt. %, generally about 2 to 40 wt. %. However, a preferred concentration of the crosslinkable composition in the aqueous medium—as well as the preferred concentration of each crosslinkable component therein—will depend on a number of factors, including the type of component, its molecular weight, and the end use of the composition. For example, use of higher concentrations of the crosslinkable components, or using highly functionalized components, will result in the formation of a more tightly crosslinked network, producing a stiffer, more robust gel. As such, compositions intended for use in tissue augmentation will generally employ concentrations of crosslinkable components that fall toward the higher end of the preferred concentration range. The appropriate concentration of each crosslinkable component can easily be optimized to achieve a desired gelation time and gel strength using routine experimentation.

Using the adhesive composition disclosed above, peel strengths ranging from approximately 2 $N/cm^2$ to approximately 10 $N/cm^2$ have been observed during in vitro testing. The test results are described in the experimental section that follows. The peel strengths achieved were similar to those observed when using DERMABOND® brand (Johnson & Johnson, New Brunswick, N.J.) 2-octylcyanoacrylate, a commercially available adhesive currently used in hernia repair. Average lap shear strengths ranging from 3.5 $N/cm^2$ to 9 $N/cm^2$ were observed in lap shear tests using BARD® mesh on cowhide. Based on these findings, were 40 $cm^2$ (4 cm×10 cm) mesh glued with the adhesive composition of the inventive method for hernia repair, it would require a force ranging from approximately 140 N (14 kg of weight force) to 360 N (36 kg of weight force) to dislodge the entire mesh from the site.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains. All patents, patent applications, patent publications, journal articles, and other references cited herein are incorporated by reference in their entireties.

The following examples are included so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C., and pressure is at or near atmospheric.

EXAMPLE 1

Comparative Peel and Lap Shear Testing

In vitro peel and lap shear tests were conducted to demonstrate the utility of the claimed adhesive materials for hernia repair applications. Adhesive materials were applied on a 2 cm×2 cm area to glue two surfaces together. The glued surfaces were incubated in phosphate buffered saline (PBS) at 37° C. for 2 hrs, then the peel strength and lap shear strength were measured on Instron Universal Tester, Model 4202, Canton Mass.

Materials

The adhesive compositions were tested on the following materials:

Polypropylene mesh: Lab grade and BARD® Mesh, Davol, Inc. Cranston, R.I.

Collagen membrane: Collagen sausage casing #1, 2, and 3, The SausageMaker, Inc., Buffalo, N.Y.

Cowhide strip: fresh cowhide strip from Spear Products, Inc., Quakertown, Pa.

The adhesive compositions were prepared as follows:

Composition A:

Component I 100 mg pentaerythritol polyethylene glycol ether tetra-succinimidyl glutarate, (MW, 10K); Shearwater Polymers, Huntsville, Ala. and 100 mg pentaerythritol polyethylene glycol ether tetra-sulfhydryl Shearwater Polymers, (MW, 10K) Huntsville, Ala., in a syringe.

Component II 1 ml of 20 mg/ml methylated collagen in a separate but connected syringe.

Methylated collagen was prepared by a modification of the procedure of Miyata et al, U.S. Pat. No. 4,164,559. A dispersion (3% w/v) of bovine pepsinized reconstituted collagen in 0.02M sodium phosphate, 0.13M NaCl, pH 7.2 (prepared by the method of McPherson et al., *Collagen Rel. Res.* 5, 119-135, 1985) was extruded onto a nonsticky glass surface in a thin string and dried at room temperature. Methanolic HCl was prepared by adding 10.7 ml of conc. HCl to 1300 ml of anhydrous methanol. The dried collagen was cut into 1×5 cm strips and added to the methanolic HCl (200 ml methanolic HCl: 1 g dry collagen) in a sealed vessel and gently shaken at 25° C. for 3 days. The methanolic HCl was carefully decanted off and the collagen was filtered on a sintered glass funnel to remove traces of methanol. Complete methanol and acid removal was completed under vacuum overnight or dialysis against $H_2O$ extensively. The methylated collagen was re-solubilized in 20 mM acetate buffer, and the pH was adjusted to 4 to 6. The amount of buffer was calculated to achieve a final protein concentration of about 20 mg/ml. Solubilized methylated collagen was a completely transparent material, free of fibers or opalescence, having a viscous, gel-like consistency.

Components I and II were thoroughly mixed between the two syringes through the connector, and this composition was then applied to the surface of the test material and spread evenly to a thickness of 0.1 ml of the mixture per cm² area to be glued. A pH 9.6 NaH$_2$PO$_4$/Na$_2$CO$_3$ buffer was applied drop-wise to the Composition A coating on the mesh. After allowing the coated, buffered mesh to stand at room temperature for 20 minutes, the mesh coating was rinsed thoroughly with PBS to remove the buffer.

Composition B

Component I 100 mg pentaerythritol polyethylene glycol ether tetra-succinimidyl glutarate; and 100 mg pentaerythritol polyethylene glycol ether tetra-sulfhydryl, in one syringe.

Component II 1 ml of 20 mg/ml methylated collagen prepared as discussed above in another syringe.

Component III 38 mg poly(L-lactic acid) fiber (PLLA) Transome, Inc., Palm Bay, Fla., washed with isopropyl alcohol and treated with H$_2$O$_2$.

Components I, II, and III were thoroughly mixed in a beaker, 0.1 ml of the mixture per cm² area to be glued was applied and then spread evenly on the surface of the test material. A pH 9.6 NaH$_2$PO$_4$/Na$_2$CO$_3$ buffer was applied drop-wise on top of the coated surface to cover the coated surface. After allowing the coated, buffered surface to stand at room temperature for 20 min, the coated test material was rinse thoroughly with PBS to remove the buffer.

DERMABOND®: 2-Octylcyanoacrylate

TISSEEL: fibrin glue.

KRAZY GLUE®: Ethyl Cyanoacrylate

Methylated Collagen: 20 mg/ml prepared as discussed above.

Pentaerythritol Polyethylene Glycol Ether Tetra-Succinimidyl Glutarate/Pentaerythritol Polyethylene Glycol Ether Tetra-Sulfhydryl: 100 mg/100 mg in 1 ml.

ZYDERM® Collagen Implant II: 65 mg/ml fibrillar collagen in PBS.

EXAMPLE 2

Figure 11:
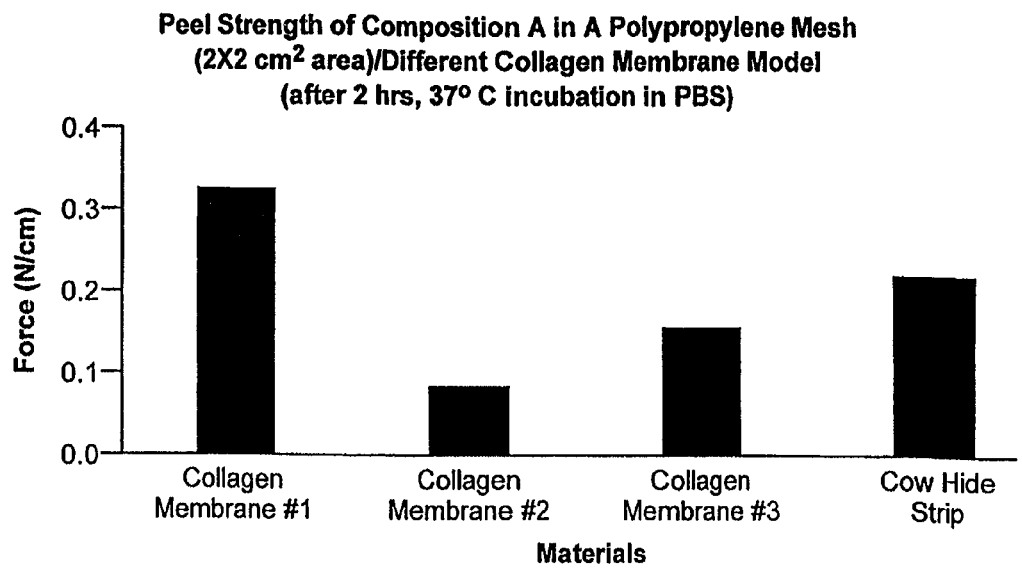
FIG. 11 presents the results of a comparative peel strength test for an adhesive composition of the invention in a 2×2 cm polypropylene mesh/collagen membrane test.

Comparative Peel Strength in 2×2 cm Polypropylene Mesh/Collagen Membrane Testing The surface characteristics of the materials used in the test model require standardization to give consistent results. Four types of collagen membrane surfaces gave different peel strength results with lab grade polypropylene mesh for the same Composition A formulation. The data are shown in FIG. 11. The affixed mesh/collagen membranes were incubated for 2 hours at 37° C. in PBS.

EXAMPLE 3

Figure 12:
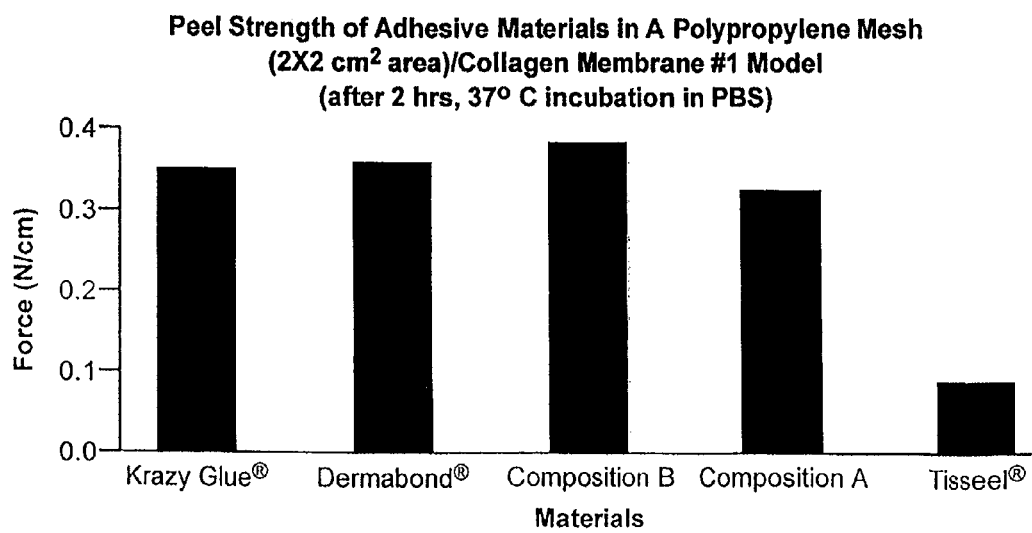
FIG. 12 graphically illustrates the results of peel strength testing for various adhesives when used to adhere lab grade polypropylene mesh to a collagen membrane surface as described in Example 3.

Comparative Peel Strength in 2×2 cm Polypropylene Mesh/Collagen Membrane Testing The peel strength for the various adhesives when used to adhere lab grade polypropylene mesh to a collagen membrane surface was determined. The amount of force required to peel the lab grade polypropylene mesh off of the membrane surface glued by different materials after incubation in PBS for 2 hrs at 37° C. varied from zero to ~0.35 N/cm linear widths. Composition A and Composition B gave the same peel strength as KRAZY GLUE® and DEREMABOND®, cyanoacrylate products. TISSEEL® gave lower peel strength, <0.1 N/cm linear width. The data are shown in FIG. 12.

EXAMPLE 4

Figure 13:
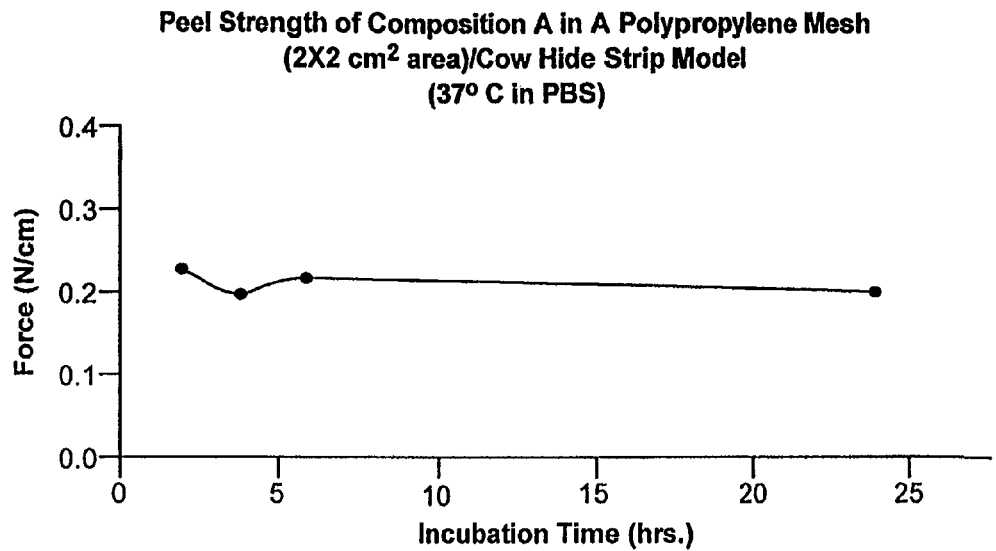
FIG. 13 graphically illustrates the changes in peel strength over a 24-hour period when an adhesive of the invention was used to affix lab grade polypropylene mesh to a cowhide strip as described in Example 4.

Comparative Peel Strength for Various Incubation Times for Compound A in 2×2 cm Polypropylene Mesh/Cowhide Strip Testing Changes in the peel strength of Composition A when used to affix polypropylene mesh to a cowhide strip did not change significantly after 24 hrs incubation in PBS at 37° C. The data are shown in FIG. 13.

EXAMPLE 5

Figure 14:
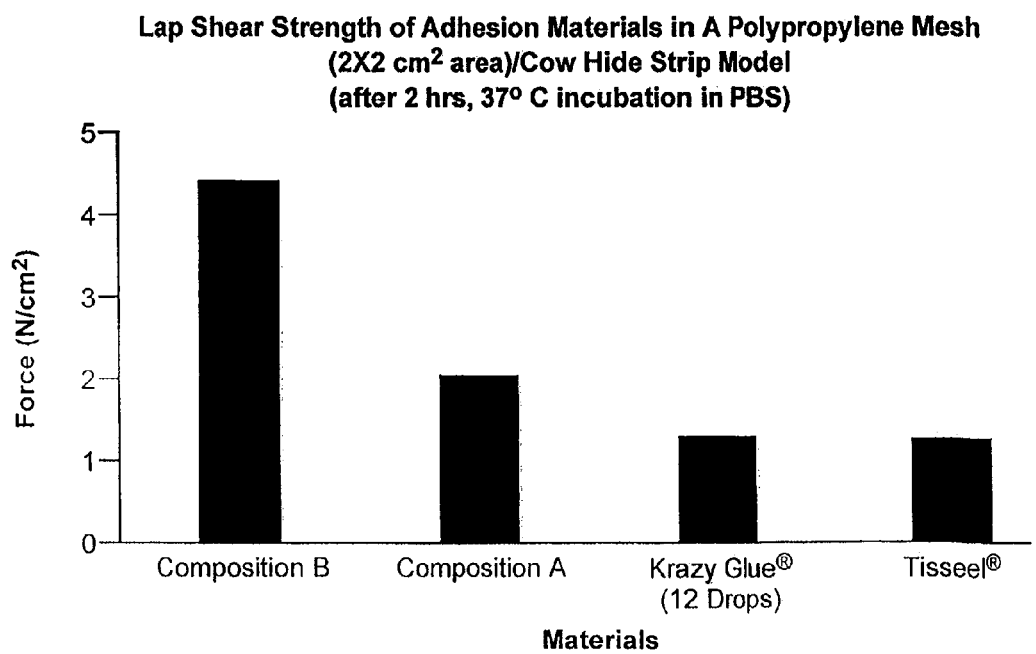
FIG. 14 graphically illustrates the results of an adhesive composition comprised of pentaerythritol polyethylene glycol ether tetra-succinimidyl glutarate, pentaerythritol polyethylene glycol ether tetra-sulfhydryl, and methylated collagen, an adhesive composition comprised of pentaerythritol polyethylene glycol ether tetra-succinimidyl glutarate, pentaerythritol polyethylene glycol ether tetra-sulfhydryl, poly (L-lactic acid) fiber, and methylated collagen, KRAZY GLUE® (Toagosei Co., Ltd., Tokyo Japan) and TISSEEL® (Immuno, Aktiengesellschaft für Chemischmedizinische Produkte, Postfach Austria) when used to affix a 2×2 cm polypropylene mesh strip onto a cowhide strip.

Comparative Lap Shear Strength for Various Incubation Times for Compound A in 2×2 cm Polypropylene Mesh/Cowhide Strip Testing The lap shear strength of Composition A, Composition B, KRAZY GLUE®, and TISSEEL® when used to affix a 2×2 cm polypropylene mesh strip onto a cowhide strip. The average pull strength for Composition A and Composition B was 2 N/cm² and 4.5 N/cm² respectively in a lab grade polypropylene mesh on cowhide strip model. The average lap shear strength of Composition B is statistically significantly higher than KRAZY GLUE® and TISSEEL®'s average lap shear strength, 1.3 N/cm² in this model. The average lap shear strength of Composition A is also higher than KRAZY GLUE® and TISSEEL®'s average lap shear strength of 1.3 N/cm², but it is not statistically significant in this model. The data are shown in FIG. 14.

EXAMPLE 6

Figure 15:
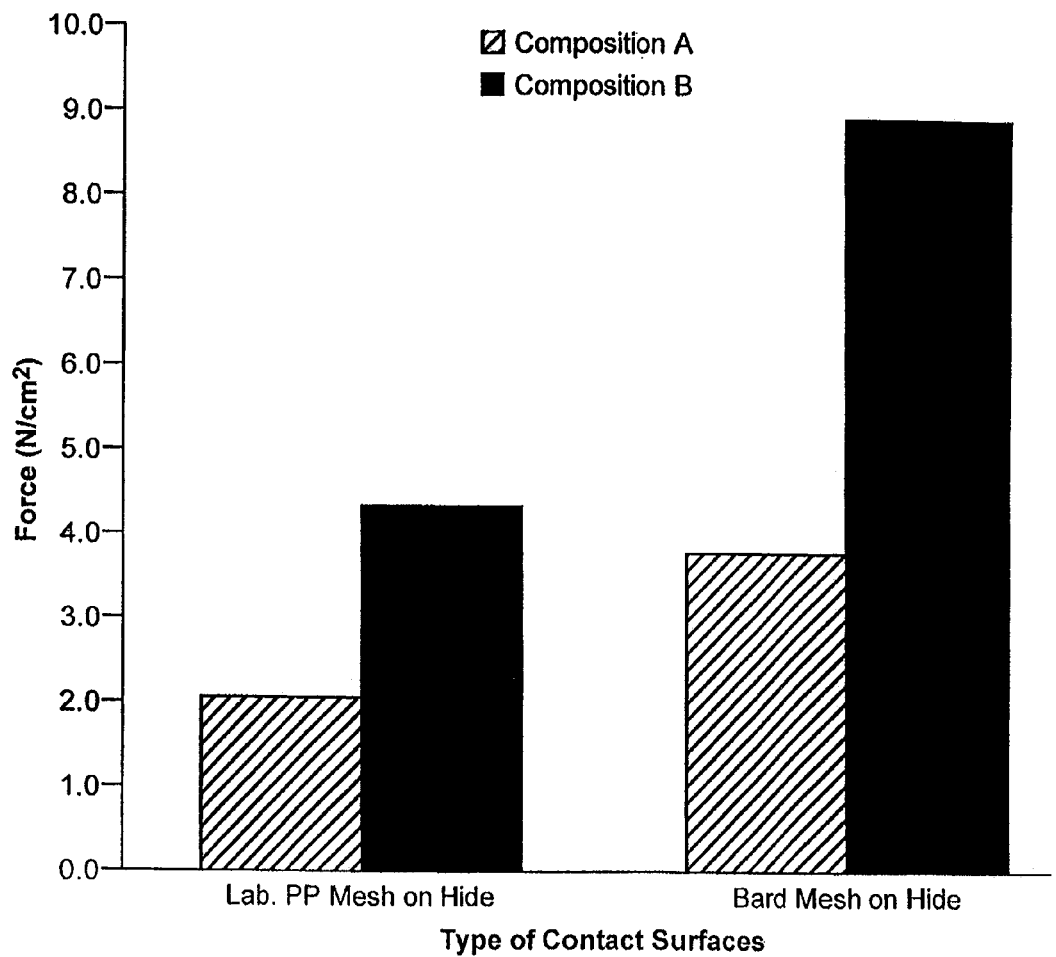
FIG. 15 graphically illustrates the results of comparative pull strength testing for an adhesive composition comprised of pentaerythritol polyethylene glycol ether tetra-succinimidyl glutarate, pentaerythritol polyethylene glycol ether tetra-sulfhydryl, and methylated collagen and an adhesive composition comprised of pentaerythritol polyethylene glycol ether tetra-succinimidyl glutarate, pentaerythritol polyethylene glycol ether tetra-sulfhydryl, poly(L-lactic acid) fiber, and methylated collagen when used to affix a 2×2 cm patch of BARD® (C.R. BARD, INC., Murray Hill, N.J.) polypropylene mesh to a cowhide strip as described in Example 6.

Comparative Lap Shear Strength for Compound A and Compound B in 2×2 cm Lab Polypropylene Mesh or BARD® Mesh/Cowhide Strip Testing The lap shear strength of Composition A and Composition B when used to affix lab grade polypropylene mesh and BARD® polypropylene mesh on cowhide strip was determined. The lap shear strength of Composition A increased from ~2 N/cm² when used with lab grade mesh to ~3.5 N/cm² when used with BARD® mesh. Similarly, the pull strength of Composition B increased from ~4.5 N/cm² with lab grade mesh to ~9.0 N/cm² with BARD® Mesh. The data are shown in FIG. 15. As Composition B contains additional PLLA fibers, interaction of the fibers with surfaces having interlocking mechanisms such as the BARD® Mesh served to increase increased lap shear strength.

EXAMPLE 7

Pentaerythritol Polyethylene Glycol Ether Tetra-Succinimidyl Glutarate/Pentaerythritol Polyethylene Glycol Ether Tetra-Sulfhydryl/Methylated Collagen Plus the Fibrous Fillers Glass Wool or VICRYL®

Materials:

Methylated Collagen, prepared as described in Example 1:

Adhesive Without Filler:

For 0.5 ml of adhesive, 50 mg of dry powdered pentaerythritol polyethylene glycol ether tetra-succinimidyl glutarate and 50 mg of dry powdered pentaerythritol polyethylene glycol ether tetra-sulfhydryl were mixed with 400 mg of methylated collagen at 31 mg protein/ml, pH 4. Both PEG components dissolved in the aqueous solution of collagen, yielding a transparent, viscous fluid. The solution was spread on the tissue site with a spatula; it flowed very little under the force of gravity. To cure the adhesive, 20-50 µl of a buffer (either 134 mM sodium phosphate, 166 mM sodium carbonate, pH 8.9; or $NaH_2PO_4/Na_2CO_3$ buffer, pH 9.6) was added to the surface. The buffer did not dilute the gel, but slowly soaked in. In 3-5 min, the surface of the gel was noticeably hardened.

For studies of bond strength under hydrated conditions, the gel plus substrate was allowed to cure for 20 min on the bench, then immersed in 50 mM sodium phosphate, 130 mM sodium chloride, pH 6.7, at 37° C. for 2 hours or longer. Testing of bond strength was performed on a tensile apparatus.

Adhesive with Filler:

VICRYL® is a copolymer of glycolic acid and lactic acid (90:10) sold as an implantable mesh by Ethicon Corporation (Polyglactin 910; Sommerville, N.J.). To the methylated collagen was added 19 mg of VICRYL® threads 1-2 cm long which had been unraveled from implantable VICRYL® mesh. In some cases, VICRYL® fibers as short as 0.3 cm were also used. The threads and the viscous gel were blended, and then the PEG components were added, as described above. Application to the tissue site and curing were as above. Other fillers and their respective amounts added to 0.5 ml of adhesive were: glass wool, 9 mg; fibrous collagen (Semed F collagen, Kensey-Nash Corporation) 8 mg; Dexon S (poly glycolide lactide sutures, "4-0"), 10 pieces 1 cm long; elastin fibers (bovine neck ligament, 0.25 to 10 mm, Elastin Products Co., Inc, Owensville, Mo.), 40 mg; stainless steel fibers (Bekaert Fibre Technologies, Marietta, Ga.), 14-28 mg (Fibers were washed with water or 1N HCl to remove a polyvinylalcohol coating); polylactide/glycolide micro-particles, prepared from polylactide/glycolide (65:35, 40-75,000 mol. wt., Aldrich Chemical Co., micro-particles 2-4 diameter prepared by the method of Zheng, J. and Hornsby, P. J., *Biotechnol. Progr.* 15, 763-767 (1999)), 25 mg.

Adhesive with Methylated Collagen Replaced by Another Agent:

Various long-chain molecules were tested, such as hyaluronic acid (rooster comb, Sigma Chemical Co., St. Louis, Mo.), chitosan (Sigma), and polylysine (Sigma). For hyaluronic acid, the formula was: pentaerythritol polyethylene glycol ether tetra-succinimidyl glutarate, 50 mg, pentaerythylene glycol ether tetra-sulfhydryl, 50 mg, VICRYL®, 14 mg, and 400 µl of hyaluronic acid, 2% (w/v) in water, pH adjusted to 4; for chitosan, the same formula, with 400 µl of 1% chitosan (w/v) in water, pH 4-5. For polylysine, pentaerythritol polyethylene glycol ether tetra-succinimidyl glutarate, 40 mg, pentaerythritol polyethylene glycol ether tetra-sulfhydryl, 30 mg, dissolved together in 50 µl water; polylysine hydrobromide, 330K, 40 mg dissolved in 60 µl water; the two solutions were mixed together, and 7 mg VICRYL® fibrils were added. In addition, polylactide/glycolide particles, prepared as above, were tested as a replacement for methylated collagen; 16.5 mg of particles were suspended in 300 µl of water and mixed with 50 mg pentaerythritol polyethylene glycol ether tetra-succinimidyl glutarate, 50 mg pentaerythritol polyethylene glycol ether tetra-sulfhydryl, and 14 mg VICRYL®. All gels were cured with pH 9.6 buffer overlay, as described above.

Adhesive without Filler and without Methylated Collagen:

Pentaerythritol polyethylene glycol ether tetra-succinimidyl glutarate was dissolved in water at 20% (w/v); pentaerythritol polyethylene glycol ether tetra-sulfhydryl was dissolved at 20% in pH 8.9 buffer. The two solutions were rapidly mixed and extruded onto the site. Gelation occurred in ~40 sec.

Mechanical Tests:

Bond strengths of the adhesive formulations were determined for each of the compositions when applied to three types of tissue or tissue surrogates. Collagen membranes (sausage casings; The SausageMaker, Inc., Buffalo, N.Y.) were washed with isopropyl alcohol and water to remove lipid and salt impurities, and dried. Bonding of membranes with a 1-3 mm overlap and a 1 cm width was performed by spreading the adhesive over the top of the sheets. Adhesive was allowed to cure 20 min on the bench and then immersed for 30 min to 2 hours at 37° C. before pulling apart in an Instron model 4202 test apparatus (Canton, Mass.), using a 100N load cell. Bonding of porcine carotid arteries (10b, Pelfreeze, Rogers, Ark.) was also performed in an end-to-end geometry. Cut carotid artery segments were abutted (4-6 mm diameter) and spread with adhesive; no stay sutures were applied. Incubation and testing were the same as described for the collagen membranes.

For bonding of cowhide strips (10c), de-haired calfskin pieces were purchased from Spear Products, Inc., Quakertown, Pa. Pieces were nearly uniform in thickness, 2-3 mm. Strips 0.4 cm wide were cut from the hide pieces, using a single-edged razor blade. Cut strips were abutted end-to-end and bonded by spreading 0.25 ml of Composition A adhesive or a few drops of cyanoacrylate. Incubation and testing were the same as described for the collagen membranes. Table 3 below shows that pentaerythritol polyethylene glycol ether tetra-succinimidyl glutarate/pentaerythritol polyethylene glycol ether tetra-sulfhydryl/methylated collagen, when filled with glass wool (Formula c), was superior in bonding strength to unfilled Formulas a and b when tested on collagen membranes. A medical grade cyanoacrylate (DERMABOND®) formed even stronger bonds with collagen membranes (5.2±1.9 N force for 7 determinations).

TABLE 3

Bonding Performance With and Without Methylated Collagen and a Fibrous Filler

| Formula | Bond Strength (N Force) | n |
|---|---|---|
| Pentaerythritol Polyethylene Glycol Ether Tetra-Succinimidyl Glutarate/Pentaerythritol Polyethylene Glycol Ether Tetra-Sulfhydryl (20%) | 1.6 ± 1.1 | 3 |
| Pentaerythritol Polyethylene Glycol Ether Tetra-Succinimidyl Glutarate/Pentaerythritol Polyethylene Glycol Ether Tetra-Sulfhydryl/methylated collagen | 1.7 ± 1.0 | 4 |
| Pentaerythritol polyethylene Glycol Ether Tetra-Succinimidyl Glutarate/Pentaerythritol Polyethylene Glycol Ether Tetra-Sulfhydryl/methylated collagen/glass wool | >2.8 ± 0.6* | 6 |

*Collagen membrane tore, but sealant bond was still intact.

TABLE 4

Bond Strength of Cyanoacrylate (KRAZY GLUE ®, Elmer's Products) on Three Different Tissue Substrates

| Substrate | Bond Strength (N Force) |
|---|---|
| Cowhide strips | 10.9, 16.2 |
| Porcine carotid artery | 2.0, 3.8 |
| Collagen membrane | 3.0 ± 1.0 (n = 5) |

Table 5 below presents data on the addition of a different filler, VICRYL® threads, to the pentaerythritol polyethylene glycol ether tetra-succinimidyl glutarate/pentaerythritol polyethylene glycol ether tetra-sulfhydryl/methylated collagen. With substrates such as cowhide or carotid artery, the substrate did not tear, and the bond strength values were representative for the strength of the adhesive bond itself. Typically these bonds failed adhesively, that is, the tensile strength of the adhesive gel itself remained intact and was not the limiting factor. The bond strengths observed in Saline at 37° C. again were comparable to those seen with cyanoacrylate for bonding the same set of tissue substrates (Table 4).

TABLE 5

Bond Strength of Pentaerythritol Polyethylene Glycol Ether Tetra-Succinimidyl Glutarate/Pentaerythritol Polyethylene Glycol Ether Tetra-Sulfhydryl/Methylated Collagen with VICRYL ® Threads as a Filler on Three Different Tissue Substrates

| Incubation Time (Hrs.) | Bond Strength (N Force) | Substrate* |
|---|---|---|
| 2 | 6.6, 5.6 | Cowhide |
| 17 | 6.3, 5.5 | Cowhide |
| 2 | 4.3, 2.2, 2.8, 5.1 | Porcine Carotid Artery |
| 2 | >5.9, 3.9 | Collagen Membrane |

*cowhide strips, 0.5 cm wide, porcine carotid artery, 0.3-0.5 cm diameter, collagen membrane: sausage casing, 0.2 mm thick, 1 cm width.

Effect of Different Fillers:

Table 6 presents results of various filler materials. Testing was performed on cowhide strips, immersed for 2 hours in saline at 37° C. It appeared that filamentous materials were more effective than spheroidal particles. Bonding of the filler to the gel is very important for improvement of strength. Collagen-polyethylene glycol filaments were waxy and did not adhere to the gel; thus, despite their high aspect ratios, they were not effective fillers.

TABLE 6

Effect of Different Fillers on Bond Strength of Pentaerythritol Polyethylene Glycol Ether Tetra-Succinimidyl Glutarate/Pentaerythritol Polyethylene Glycol Ether Tetra-Sulfhydryl/Methylated Collagen

| Material | Bond Strength (N Force) |
|---|---|
| VICRYL ® | 4.7, 7.4 |
| VICRYL ®, washed with ethanol | 7.2, 7.8 |
| VICRYL ®, treated with ethanol, then washed with 30% hydrogen peroxide | 8.3, 9.1 |
| Surgical silk sutures 1-2 cm long, 30-50μ diameter | 2.5, 3.8 |
| Surgical silk sutures, unraveled to finer threads, washed with chloroform | 5.0, 6.5 |
| Fibrous collagen (Semed F, Kensy-Nash) adjusted to pH 4; 0.5 to 1 mm long, ~50μ diameter | 1.3, 2.8 |
| Gelatin particles, cross-linked by heat, ~100μ diameter, polygonal | 0.6, 0.8 |
| Hydroxyapatite particles, 0.5 to 1 mm diam. polygonal | 0.7 |
| Collagen-polyethylene glycol conjugate filament ~50μ diameter, 1 cm long | 0.8, 1.7 |
| Stainless steel fibers 8μ diameter, 4 mm long | 4.8, 6.9 |
| Elastin fibers 0.25 to 10 mm long | 3.9, 4.0 |
| Polylactide/glycolide particles, 2-4μ diameter | 1.1, 1.1 |

Effect of Cross-Linking Bond:

Table 7 below shows that when the gel was formed from other types of cross-linking reactions, the adhesion and bond strength was affected when tested on cowhides after incubation at 37° C. Material 1 was formed from pentaerythritol polyethylene glycol ether tetra-sulfhydryl and hydrogen peroxide, which oxidizes adjacent sulfhydryl groups to a disulfide bond. A gel forms rapidly, and the gel can be supplemented with methylated collagen and VICRYL® (Johnson & Johnson, New Brunswick, N.J.); however, after several hours in saline buffer, the gel becomes very weak; the VICRYL® fibers are easily pulled out. Material 2 utilized the reaction of sulfhydryl groups from pentaerythritol polyethylene glycol ether tetra-sulfhydryl with the double bond of a 4-arm vinyl sulfone derivative of PEG (10K, Shearwater Polymers). The presumed reaction, a Michael-type addition, formed a thio-ether bond. Such gels had adequate tensile strength but poor adhesion to the cowhide after incubation in saline. Materials 3 and 4 contained (pentaerythritol polyethylene glycol ether tetra-amine, 10K, Shearwater Polymers); the amino functionality presumably reacted with the succinimidyl ester of pentaerythritol polyethylene glycol ether tetra-succinimidyl glutarate to form an amide linkage. These gels were comparable in performance to those formed from pentaerythritol polyethylene glycol ether tetra-succinimidyl glutarate and pentaerythritol polyethylene glycol ether tetra-sulfhydryl. (For proper reaction in the presence of methylated collagen, the pentaerythritol polyethylene glycol ether tetra-amine had to be titrated to pH 2-4 during the mixing of reagents; on addition of curing buffer, its pH was increased, permitting the reaction of the amino group). It appeared that the presence of the succinimidyl ester was important for achieving the highest adhesion to the tissue substrate and for good tensile strength of the gel. Other groups that react with amines, such as aldehydes (aldehydes conjugated to multi-armed PEG), are also anticipated to be effective adhesive-forming reagents.

TABLE 7

Bond Strengths of Various Functionalized PEGs Filled with VICRYL ® Threads

| Material No. | Material | Incubation Time (Hrs.) | Bond (N Force) |
|---|---|---|---|
| 1 | Pentaerythritol Polyethylene Glycol Ether Tetra-Sulfhydryl/Methylated Collagen/VICRYL ®/H$_2$O$_2$ | 17 | 0.32, 0.20 |
| 2 | Pentaerythritol Polyethylene Glycol Ether Tetra-Sulfhydryl/4arm vinyl 2 sulfone PEG/Methylated Collagen/VICRYL ® threads | 2 | 2.2, 1.5 |
| 3 | Pentaerythritol Polyethylene Glycol Ether Tetra-Succinimidyl Glutarate/Pentaerythritol Polyethylene Glycol Ether Tetra-Sulfhydryl/Pentaerythritol Polyethylene Glycol Ether Tetra-Amine/Methylated Collagen/VICRYL ® threads | 2 | 6.4 |
| 4 | Pentaerythritol Polyethylene Glycol Ether Tetra-Succinimidyl Glutarate/Pentaerythritol Polyethylene Glycol Ether Tetra-Amine/Methylated collagen/VICRYL ® threads | 4 | 3.6, 6.4 |
| 4 | Pentaerythritol Polyethylene Glycol Ether Tetra-Succinimidyl Glutarate/Pentaerythritol Polyethylene Glycol Ether Tetra-Amine/Methylated collagen/VICRYL ® threads | 2 | 6.6, 5.6 |

Persistence of the Bond Under Hydrated Conditions:

Table 8 shows that the adhesives formed from pentaerythritol polyethylene glycol ether tetra-succinimidyl glutarate, pentaerythritol polyethylene glycol ether tetra-sulfhydryl, and also pentaerythritol polyethylene glycol ether tetra-amine form bonds using cowhide that persist for long times immersed in saline buffer at 37° C. Such stringent hydrated conditions simulate the in vivo environment. Bond weakening was observed after more than 100 hours of hydration. The weakening of bond strength was thought to be due to hydrolysis of carboxyl-ester and thio-ester network linkages. Pentaerythritol polyethylene glycol ether tetra-succinimidyl glutarate is a glutaryl-succinimidyl ester; even after reaction with the terminal carboxyl of the succinimidyl ester, there remains a carboxyl ester linking the glutaryl moiety to the main PEG chain; this bond, as well as the thio-ester bond, could hydrolyze.

TABLE 8

Bond Performance Under Long Hydration Times

| Material | Incubation Time (Hrs.) | Bond Strength (N Force) |
|---|---|---|
| Pentaerythritol Polyethylene Glycol Ether Tetra-Succinimidyl Glutarate/Pentaerythritol Polyethylene Glycol Ether Tetra-Sulfhydryl/Pentaerythritol Polyethylene Glycol Ether Tetra-Amine/Methylated collagen/VICRYL ® threads | 2 | 6.4 |
| | 66 | 2.6, 4.1 |
| | 70 | 3.0 |
| | 137 | 0.70, 2.6 |
| | 140 | 1.1, 0.4 |
| Pentaerythritol Polyethylene Glycol Ether Tetra-Succinimidyl Glutarate/Pentaerythritol Polyethylene Glycol Ether Tetra-Amine/Methylated collagen/VICRYL ® threads | 4 | 3.6, 6.4 |
| | 64 | 7.0, 5.1 |
| | 136 | 3.8, 2.7 |
| | 234 | 2.7, 1.7 |
| Pentaerythritol Polyethylene Glycol Ether Tetra-Succinimidyl Glutarate/Pentaerythritol Polyethylene Glycol Ether Tetra-Sulfhydryl/Methylated collagen/VICRYL ® threads | 2 | 6.6, 5.6 |
| | 17 | 6.3, 5.5 |
| | 69 | 0.63, 0.90, 3.4, 5.4 |
| | 93 | 2.4, 5.4 |
| | 140 | 3.2, 2.9 |
| | 235 | >2.4, 3.7 |

Related Formulas with Lower Molecular Weight Compounds Bearing Succinimidyl Ester and Amino or Thiol Reactive Groups:

Table 9 presents bond strengths on cowhide strips of lower molecular weight PEG derivatives as adhesives, again supplemented with methylated collagen and VICRYL®. Tri-functional succinimidyl-succinate of a 3-armed PEG built from a glycerol core, 2600 mol. wt., was obtained from NOF Corporation, Japan and 4-armed polyethylene glycol di-amine, 2000 mol. wt., was obtained from Shearwater Polymers. The polymers were VICRYL® filling appeared to have a small effect on bond strength. The following proportions were used: methylated collagen, 500 µl (22 mg/ml in water 2707-30B); tri-functional succinimidyl-succinate of a 3-armed PEG built from a glycerol core, 48 mg; 4-armed polyethylene glycol di-amine, 2000 mol. wt., Shearwater Polymers, 60 µl of 60% solution in water, titrated to pH 1-2 with 6M HCl; VICRYL® threads, 26 mg.

TABLE 9

Low Molecular Weight Analogues to Pentaerythritol Polyethylene Glycol Ether Tetra-Succinimidyl Glutarate and Pentaerythritol Polyethylene Glycol Ether Tetra-Sulfhydryl

| Materials | Incubation Time (Hrs.) | Bond Strength (N Force) |
|---|---|---|
| Tri-functional succinimidyl-succinate of a 3-armed PEG built from a glycerol core/4-Armed Polyethylene Glycol Di- | 2 | 2.3, 0.64 |

TABLE 9-continued

Low Molecular Weight Analogues to Pentaerythritol Polyethylene Glycol Ether Tetra-Succinimidyl Glutarate and Pentaerythritol Polyethylene Glycol Ether Tetra-Sulfhydryl

| Materials | Incubation Time (Hrs.) | Bond Strength (N Force) |
|---|---|---|
| Amine/Methylated Collagen Tri-functional succinimidyl-succinate of a 3-armed PEG built from a glycerol core/4-armed polyethylene glycol di-amine, 2000 mol. wt., Shearwater Polymers/Methylated Collagen/VICRYL ® threads | 5 | 2.3, 3.3 |

EXAMPLE 8

Lap Shear Testing of the Adhesive of the Invention vs. TISSUCOL®

The mechanical strength of an adhesive of the invention and TISSUCOL® (Immuno Aktiengesellschaft, Wien, Austria) were evaluated using a survival rat flap model. Composition A, as described in Example 1, was used as the adhesive and delivered with a CoStasis cannula. Data from 14 animals is reported: 7 rats per the adhesive group and 7 rats per TISSUCOL® group. A 2×3 cm skin flap was made on the chest of each rat. The lap shear force (N/cm2) required to detach the mesh was measured. The mean force for the adhesive of the invention at 3 days was 1.1±0.06 N/cm2. The mean peel force for TISSUCOL® at 3 days was 1.57±0.54 N/cm2. Mechanical test results were evaluated by non-parametric Wilcoxon/Kruskal-Wallis analysis and Tukey-Kramer HSD parametric analyses to determine p-values for significance. Composition A and TISSUCOL® were not statistically significantly different. The data from this study demonstrate that Composition A is mechanically as strong as TISSUCOL®.

Methods:

This study included a total of 14 rats, divided into four treatment groups. A 2×3 cm skin flap was made on the chest of a rat. Once the skin flap was raised, 0.4 mL of Composition A was placed onto the muscle using a cannula. The mesh was laid down over the material and counter buffer was sprayed on to initiate crosslinking of the adhesive. The tissue closed after 2 minutes using staples in the same manner for all groups. The animals were euthanized 3 days after application. The staples used for closure of the surgical site were removed for mechanical testing. For mechanical testing, the euthanized rats were secured onto a board with straps. The end of the mesh was raised and placed in a clip attached to the upper jig of the Instron, Model 4202 Serial #246 (Collagen Corp Asset #1225). The Instron was setup for measuring tension. The speed was set at 10 mm/min using a 100 Newton Load Cell. The grip pulls up on the skin separating it from the muscle. The mesh pulls apart from the muscle leaving a thin layer of the adhesive on both the mesh side and the muscle side.

Statistical Method:

The average and standard deviations (SD) for peel strength (N/cm) for each group were determined using raw data. Mean peel strengths were evaluated by nonparametric Wilcoxon/Kruskal-Wallis Tests (Rank Sums) and Tukey-Kramer HSD parametric analyses to determine p-values for significance. All analyses were performed using JMP statistical package, version 3.0 (SAS Institute).

Results:

The biological response to Composition A and TISSUCOL® was evaluated. Overall, Composition A and TISSUCOL® as well as the hernia mesh seemed biocompatible at 3-days post implantation. Each of the adhesives flowed into the mesh spaces and could be seen histologically at 3 days.

The strength of attachment was measured at three days post implantation. Composition A showed a lap shear of 1.11 N/cm$^2$ with a standard deviation of 0.06, while the TISSUCOL® demonstrated a lap shear of 1.57 N/cm$^2$ with a standard deviation of 0.54. Although the mean for TISSUCOL® is higher than that of the adhesive of the invention, there is not a statistically significant difference between the two groups. Composition A was not statistically significantly stronger than TISSUCOL®, $p \geq 0.05$ (Tukey-Kramer). Also, adhesions, mesh to skin, were found in every case with TISSUCOL® whereas Composition A had no adhesions.

EXAMPLE 9

Lap Shear Testing of Hernia Mesh Attached with Composition A and TISSUCOL® In Vivo Rats were implanted in the ventral thoracic region with hernia mesh coated with either Composition A or TISSUCOL®. Animals were sacrificed 3-days post operative and the implants subjected to mechanical testing and/or prepared for microscopic evaluation. Both of the composites were biocompatible showing only a few macrophages on the surface of the attachment materials and in surrounding subcutaneous tissues. Polymorphonuclear neutrophils penetrated TISSUCOL® making it appear porous; however, Composition A was generally acellular. The latter properties of the two materials could affect their individual turnover rates and the time course of tissue in growth necessary for hernia mesh fixation.
Materials and Methods:

Eleven rats were implanted in the mid-thoracic region with a composite of either hernia mesh/Composition A or a hernia mesh/TISSUCOL®. The implants and surrounding tissues were harvested at 3-days post implantation and processed for paraffin and glycolmethacrylate (GMA) plastic embedding either before or after mechanical testing. In most cases, the composite implants and the surrounding tissues were embedded in separate blocks. Paraffin sections were stained with hematoxylin and eosin (H & E) and Masson's trichrome stain; plastic sections were stained with H & E only. A total of 50 slides from the sites were evaluated microscopically for presence, site, and cellularity of the implant materials. The appearance of serum pockets and types of inflammatory cells were also noted. Observations were recorded and used as the basis for this text.
Results:

There was no tissue reaction in the skin above the implant sites. Low to moderate numbers of macrophages was present in the subcutaneous tissues associated with both the hernia mesh/Composition A and the hernia mesh/TISSUCOL® composites. Serum pockets containing fibrin and blood were also seen in the subcutaneous layer. These probably resulted from creating and elevating the skin flaps for placements of the implants.

After mechanical testing, both Composition A and TISSUCOL® stayed with the mesh with little, if any, material remaining attached to the host tissues. A small amount of tissue was sometimes associated with the TISSUCOL®/mesh complex, but no tissue pulled way with the Composition A/mesh complex after testing. The attachment materials filled the void spaces or pores of the mesh, but there was no indication of either material or cellular penetration of the weave of the mesh. When the mesh was viewed with polarized light a layer of Composition A sometimes covered it, while the mesh was usually completely exposed in sections of TISSUCOL®. This might suggest that a thicker layer of Composition A was applied to the mesh compared to the amount of TISSUCOL® used for coating the mesh.

Composition A was completely acellular and showed no evidence of degradation at this early time point. This material elicited minimal tissue reaction with only a few macrophages and polymorphonuclear neutrophils (PMN's or neutrophils) associated with its surface. A few macrophages were also seen on the surface of TISSUCOL® however, a large numbers of polymorphonuclear neutrophils (PMN's) were observed surrounding this material. Some of the PMN's had penetrated the surface of the TISSUCOL® giving it a spongy, porous appearance.

There was no indication that the mesh was responsible for any of the cellular responses associated with the attachment materials or seen in the surrounding subcutaneous tissues. However, implants of the mesh alone would have provided a definitive answer to this question and also established baseline mechanical testing data.

The large numbers of PMN's associated with TISSUCOL® may not be cause for concern since the material contains fibrinogen and fibrinogen fragments can act as chemo attractants for these cells during normal wound healing. In addition, PMN's are often the first to appear at a site of soft tissue injury as well as following placement of an implant. Generally, if they do not persist beyond a week or two there is little cause for concern. If they persist beyond this time period then some chronic irritant on infection is likely present. Other than the PMN infiltrate associated with TISSUCOL®, tissue reactivity was mild. There was a slight increase in the number of tissue macrophages with both attachment materials. The sequential appearance of increased numbers of macrophages after PMN's peak also occurs during normal wound healing. Hence, biocompatibility does not seem to be a problem with either material at this time point.

The presence of holes in TISSUCOL® after cell penetration may suggest that it will turnover faster than Composition A that shows no cell infiltration or evidence of degradation at this early time point. The issue is whether a faster or slower turnover rate for attachment materials is more advantageous in this clinical indication. If the most important function of the attachment material is initial stabilization and the most desirable final fixation of the mesh is tissue in growth, then a material that turns over faster might be more desirable. Faster turnover might favor faster in growth and tissue fixation while an attachment material with a higher persistence might hinder penetration of host tissue.

EXAMPLE 10

High-Strength Adhesives Based on COH102 and COH206 and a Comparison with Adhesives Prepared from PETA, PESH-P, and GLYC-20HS Summary:

Several types of gels were investigated as potential suture replacement formulations. Gels based on penta-erythritol derivatives exhibited high cohesive, but poor adhesive strength. Gels based on a 3-armed succinimidyl glycerol-PEG exhibited low cohesive strength, but good adhesive strength. Gels based on 60% aqueous (w/v) COH102/COH206, to which various fibrous materials were added, such as fibrous insoluble collagen, polyglycolide sutures and glass wool, exhibited both good cohesive and adhesive strengths.

High strength medical adhesives are of interest as suture-replacements in closure of surgical incisions. In particular, gels formed from PETA and PESH-P were shown to have tensile strengths about 10× greater than those formed from 20% (w/v) solutions of COH102 and COH206. When PETA-PESH-P gels were supplemented with fibrous or particulate polymers, gels with even higher tensile strengths were observed.

This experiment describes the adhesive properties of PETA/PESH-P and related gels, as well as both adhesive and tensile properties of a formulation of COH102 and COH206 at 60% (w/v), to which collagen and other polymers are added. Also described are properties of gels formed from a 3-arm glycerol succinimide (NOF Corp., Japan) and the above reagents.

Materials and Methods:

COH102: penta-erythritol polyethylene glycol ether tetra succinimidyl-glutarate, 10,000 mol. wt.;

COH206: penta-erythritol polyethylene glycol ether tetra-thiol, 10,000 mol. wt.);

PETA: penta-erytlritol tetra acrylate;

PESH-P: penta-erythritol tetrakis (tri mercapto propionate);

GLYC-20HS: (poly-oxyethylene glyceryl ether) succinimidyl succinate 2600 mw);

PETA, PESH-P, and penta-erythritol tetrakis (3 mercaptoacetate) (PESH-A), polyethylene, surface activated 180μ particle size, and polybutadiene, epoxy functionalized, epoxy E.W. 260, were purchased from Aldrich Chemical Co., Milwaukee, Wis. GLYC-20HS, DEPA-10H (poly-oxyethylene bis-amine 1040 mw) were obtained from NOF Corporation, Japan. COH102 and COH206 were reagent grade from Shearwater Polymers, Huntsville, Ala. Polyethylene-co-acrylate-succinimidate (PE-AC-S) was synthesized from a polyethylene-co-acrylate (approx. mol. wt. 400K with 5% acrylate) purchased from Aldrich Chemical Company, Milwaukee, Wis. Kensey-Nash insoluble collagen (Semed F) was purchased from Kensey-Nash Corporation, Exton, Pa. Collagen Matrix, Inc, Franklin Lakes, N.J., supplied a second type of insoluble collagen. Prolene 7-0 sutures were manufactured by Ethicon Corporation. Coarse fibered collagen sheets were cut from the same coarse fibered bovine corium collagen as that used for the burst test as described in Prior, J. J., Wallace, D. G., Hamer, A., and Powers, N., "A sprayable hemostat containing fibrillar collagen, bovine thrombin, and autologous plasma", Ann. Thor. Surg. 68, 479-485 (1999). These collagen sheets served as a tissue model for further studies. Smaller fiber collagen was prepared from re-precipitated pepsin-digested bovine corium collagen manufactured by Collagen Aesthetics, Inc., Palo Alto, Calif. Glass wool was purchased from VWR Corporation. Poly-glycolide sutures, non-coated ("Dexon S") were from Davis and Geck.

For burst tests, the apparatus used is described in Wallace, et al., supra. Approximately 1 ml of total formula was sprayed or spread by spatula onto the coarse fibered collagen sheet substrate and allowed to set. Water pressure was applied after the formulation had reached the texture of a relatively firm rubbery solid (no longer tacky), and the pressure to rupture the seal was recorded as mm Hg.

60% gels of COH102 and COH206 were prepared as follows: COH102 was dissolved at 60% (w/v) in S-buffer (0.5 mM sodium phosphate, pH 6.0) and COH206 was dissolved also at 60% in 300 mM sodium phosphate at pH 7.5 or 8.9; or in 117 mM sodium phosphate, 183 mM sodium carbonate, pH 9.6 ("PC buffer"). In some cases the above ratio of phosphate and carbonate were altered to give pH 9.44 for a faster set time. The pH used in each case was determined by the rate of gelation desired. Various additives were added to such a base formulation; e.g., Kensey-Nash and smaller fiber size collagen was added at 28 mg/ml of final gel; glass wool was added at 25 mg/ml; and polyglycolide sutures, at 40 mg/ml.

Results and Discussion:

The results are discussed below and shown in Tables 10, 11, and 12 that follow. A tensile strength of >60 N/cm$^2$ is considered to be "strong". A burst strength of >50 mm Hg is considered to be "good adhesion".

However, when they were tested for adhesion to a hydrated simulated tissue (coarse fibered collagen sheets) in the burst test, they exhibited poor adhesion (<50 mm Hg burst pressure). As shown below in Table 10, the formulation was then modified to contain water soluble GLYC-20HS and DEPA-10H, or the pair COH102 and COH206 (which alone in aqueous media gave good adhesion to the collagen sheets). These materials had good tensile strength (manual evaluation), but again poor adhesion to the collagen sheets. The gel formed from GLYC-20HS and DEPA-10H also had poor adhesion when no water was present in the formula. A different result may be observed when these reagents are dissolved in aqueous buffers, since they are water soluble.

However, when GLYC-20HS was the major component by mass, the gels were weak but exhibited good adhesion in the burst test. Using these particular combinations of components, it appeared that one could achieve either high tensile strength or high adhesive bonding, but not both.

TABLE 10

Tensile strength and burst strength of gels prepared with NOF 3-arm glycerol succinimide

| Material | Tensile Strength (N/cm$^2$) | Burst Strength (mmHg) |
|---|---|---|
| PETA 500 mg<br>PESH-P 540 μl<br>T403 5 ul | >60 | 23 |
| GLYC-20HS 50 mg<br>PETA 500 mg<br>PESHP 540 μl<br>DEPA-10H 9 mg | >60 | 14.5 |
| PESH-A 216 ul<br>PETA 240 mg<br>GLYC-20HS 40 mg | >60 | 11 |
| PETA 400 mg<br>COH102 100 mg<br>PESH-P 440 μl<br>COH206 100 mg<br>DEPA-10H 8 mg | >60 | 15 |
| GLYC-20HS 640 mg<br>DEPA-10H mg | — | 25 |
| GLYC-20HS 400 mg<br>PESH-A 36 μl<br>T403 10 μl | <30 | >120 |
| GLYC-20HS 400 mg<br>PETA 50 mg<br>PESH-A 72 μl<br>T403 20 μl | <30 | 166, 194 |
| GLYC-20HS 200 mg<br>T403 19 μl<br>PESH-P 18 μl | <30 | 55 |

The ability of a succinimidyl-derivatized polyethylene (PE-AC-S) to act as an effective tensile strength enhancer for PETA-PESH-P gels and for COH102/206 gels was also assessed (Table 11). This material did not increase the tensile strength of these gels, perhaps because it was not an extended filament, i.e., its aspect ratio was not high enough.

TABLE 11

Polyethylene-co-acrylate-succinimide ("PE-AC-S") as a Tensile Strength Enhancer

| Material | Tensile Strength (N/cm$^2$) |
|---|---|
| PETA 400 mg PESH-P 432 µl T403 8 µl PE-AC-S 20 mg | 80 (same as control with no PE-AC-S) |
| COH102 COH206 (60%) + KN collagen (28 mg/ml) + PE-AC-S (40 mg/ml) | 38 (weaker than control with no PE-AC-S) |

Table 12 also summarizes results with COH102 and COH206 plus Kensey-Nash fibrillar collagen, which exhibited an enhanced tensile strength over 20% and 60% (w/v) gels of COH102/206 alone. Furthermore, the COH102/COH206/collagen formulation possessed good adhesive bonding to the collagen sheets. Other additives, such as hide grindate and Prolene 7-0 sutures also enhanced the gel strength over controls. Some fillers, such as small fiber collagen, polyethylene, and polybutadiene, did not exhibit tensile strength enhancing properties. Finally, some fillers or combinations thereof, such as glass wool and insoluble collagen plus poly-glycolide sutures, exhibited a significant enhancement of tensile strength, exceeding that seen with cyanoacrylate (385 N/cm$^2$). Limited burst strength data were collected, but they confirm that all these COH102/206 (60%) formulations are highly adhesive to collagen surfaces, and thus would be expected to adhere to tissues as well.

As shown in Table 12, the P-HEMA hydrogel is described in Santin, M., et al., "Synthesis and characterization of a new interpenetrated poly (2-hydroxyethylmethacrylate)-gelatin composite polymer", *Biomaterials* 17, 1459-1467; and the gelatin-PEG-di-acrylate is described in Nakayama, Y., and Matsuda, T., "Photocurable surgical tissue adhesive glues composed of photoreactive gelatin and poly(ethylene glycol) diacrylate", *J. Biomed. Biomat. Res.* (*Appl. Biomater.*) 48, 511-521 (1999).

TABLE 12

Tensile strength and burst strength tests

| Material | Tensile Strength (N/cm$^2$) | Burst Strength (mm Hg) |
|---|---|---|
| COH102/206 20% GEL | 2-12 | 100-200 |
| pHEMA HYDROGEL* | 3 | |
| GELATIN-PEG-DI-ACRYLATE** | 5-16 | 151 ± 34 |
| PETA-PESH-P | 50-170 | 14, 23 |
| PETA-PESH-P + KN collagen | 140-200 | |
| COH102/206 (60%) + KNcollagen | 123 ± 39 (n = 7) | 268, 216 |
| COH102/206 60%) + KNcollagen (+7-O Prolene sutures | 180 | |
| COH102/206 (60%) + hide grindate | 197, 78 94 | |
| COH102/206 (60%) no filler | 27 | |
| COH102/206 (60%) + Small fiber collagen | 27 | |
| COH102/206 (60%) + 7-O Prolene sutures coated | 58 | |
| COH102/206 (60%) + polyethylene | 14 | |
| COH102/206 (60%) + polyethylene + poly-butadiene | 58, 30 28, 21 | |
| COH102/206 (60%) + glass wool | 745 161 | 156 |
| COH102/206 (60%) + KN collagen + Dexon S sutures | 531 | |
| COH102/206 (60%) + Collagen Matrix collagen + Dexon S sutures | 718 | 376 |

EXAMPLE 11

Collagen Sheet Composites Containing Active PEG

Summary

COH102 and COH206 can be dissolved together in ethanol without reaction. The ethanol solution can be evaporated to dryness, leaving a reactive PEG powder. When placed in PC buffer, pH 9.6, the powder gels instantly. This finding was then used to develop an adhesive sheet. Collagen sponges and coarse fibered collagen sheets coated with sponges were impregnated with ethanol solutions of COH102 and COH206. After drying, such reactive PEG sheets were able to bond to a coarse fibered collagen sheet. Burst strengths of about 300 mm Hg were observed after 10 min at pH 7.

Adhesive sheets were also prepared that consisted of a coarse fibered collagen backing (prepared as described in Example 10) to which was bonded a collagen sponge. The sponge layer was impregnated with the reactive PEG powder. When such sheets were placed dry onto a second coarse fibered collagen sheet wetted with pH 9.6 buffer, a strong bond was formed in as little as 30 seconds. Bonding of the adhesive sheet to the second collagen sheet was measured by the burst test. Burst strengths up to 500 mm Hg were observed.

Materials and Methods

Coarse fibered collagen sheets were prepared as described elsewhere herein. Collagen sponges were attached to the collagen sheet by extruding a slurry of reconstituted fibrillar collagen on top. The reconstituted collagen slurry was prepared by diluting outdated Zyderm II collagen (65 mg/ml protein, Collagen Aesthetics, Inc., Palo Alto, Calif.) with water to achieve a 20 mg/ml dispersion. Approximately 7 cm$^2$ of sheet were covered per ml of slurry. Once the collagen slurry was extruded onto the coarse fibered collagen sheets, the composite was frozen and then freeze dried. After freeze-drying, a porous collagen sponge remained adherent to the collagen sheet. To the dry sponge was added dropwise an alcohol solution of COH102 and COH206. The latter was prepared by adding 200 mg of COH102 and 200 mg COH206 each to 1.8 ml of absolute ethanol (dried over molecular sieves). Dissolution of both PEG compounds in ethanol was achieved by gentle warming and stirring (up to about 40° C.).

The two solutions were then mixed. One ml of ethanol solution was used to cover about 10 cm² of sheet. The sponge-collagen sheets, wetted with the PEG solution in ethanol were then dried briefly in a vacuum chamber. When bulk solvent was gone, the sheets were transferred to a lyophilizer for several hours to remove solvent residues. The dry sheets were stored at −20° C. under dry argon.

To test bonding to a second coarse fibered collagen sheet, a burst test was performed. The test sheet of collagen was wetted with PC buffer, pH 9.6 and secured into the sample cell. Additional buffer (0.1 to 0.2 ml) was applied to the sheet. Then the active PEG sponge sheet (prepared as above; 1.2× 1.2 cm) was placed, sponge side down on the test collagen sheet (size of defect: 2 mm). The two sheets were manually held in place for 2-3 seconds to assure good contact and hydration of the active PEG sheet. Then the two sheets were left to incubate at room temperature until water pressure was applied from below. The pressure required to rupture the seal was recorded.

Results

Table 13 shows that very high bonding strengths can be achieved at pH 9.6, compared to control sheets with no active ingredients. High bond strengths are observed even at short times. The long-term stability of the bond was examined qualitatively: a bonded pair of sheets was removed from the burst test apparatus and placed in 100 ml of water at 33° C. The bond was still intact and apparently strong, even 30 hours later.

TABLE 13

Burst strengths of active PEG sheets apposed to coarse fibered collagen sheets

| Material | Incubation Time (min) | Burst Strength (mm Hg) |
|---|---|---|
| Sheet (control) | 0.5 | 5 |
| Sheet + Sponge (control) | 0.5 | 17 |
| Active PEG + Sheet + Sponge | 0.5 | 360, 391 |
| Active PEG + Sheet + Sponge | 1.0 | 477, 531 |
| Active PEG + Sheet + Sponge | 3.0 | 276, 231 |

Table 14 shows the effect of lowering the pH of the hydrating buffer. The strength of the bond was pH dependent, and much weaker bonding was observed at pH 7.5. However, bond strengths at lower pHs were improved by allowing longer (3 to 10 minutes) for bond formation, which may be acceptable for certain applications.

The mode of failure was not always evident. In some cases, the test sheet became dislodged from the test clamp without damaging the bond. These results were not reported. If the test sheet remained securely clamped, it appeared that failure was between active sheet and test sheet. In some cases, the active sheet was lifted and water spurted from the hole. In other cases, water appeared at the margins of the test cell, but its source was not clear.

TABLE 14

Burst strengths of active PEG sheets apposed to coarse fibered collagen sheets

| Material | pH* | Incubation Time (min) | Burst Strength (mm Hg) |
|---|---|---|---|
| Active PEG + Sheet + Sponge | 8.9 | 0.5 | 121 |
|  | 8.9 | 1.0 | 191 |
|  | 8.9 | 1.0 | 191 |
|  | 8.9 | 3.0 | 298 |
|  | 7.5 | 1.0 | 2 |
|  | 7.5 | 3.0 | 50 |
|  | 7.5 | 10.0 | 279 |

*pH 8.9 buffer was 300 mM sodium phosphate; pH 7.5 buffer was 300 mM sodium phosphate.

EXAMPLE 12

Additional Studies on Adhesive Sheets Containing Active PEG

Summary

Adhesive sheets were prepared from COH102/COH206, Zyderm collagen, and Kensey-Nash (Semen F) collagen. Such sheets showed good burst strengths when bonded to coarse fibered collagen sheets.

A shear failure bonding test was developed. In this test, the bond strength of active PEG adhesive sheets were comparable to cyanoacrylate (SUPERGLUE). This experiment describes the preparation of adhesive sheets from biocompatible materials, including implantable grade Kensey-Nash collagen. Also reported herein are comparative results of various formulations in a shear failure test.

Materials and Methods:

Active sheets were prepared from coarse fibered collagen sheets, reconstituted collagen, and COH102 and COH206, as described in Example 11.

Active sheets from Kensey Nash collagen were prepared as follows: collagen (4 g) was added to 200 ml of de-ionized water adjusted to pH 2 with HCl. Stirring with an overhead impeller was maintained for 6 days. The fibers became swollen and dispersed, creating an almost coherent mass. The slurry was poured into 9 cm diameter square polystyrene weighing boats (about 15 ml per boat to cover the bottom). The poured slurry was left in an incubator at 33 to 37° C. to dry. Sheets formed on the surface of the weigh boats. In some cases such sheets were coated with Zyderm collagen (slurry in water at 20 mg/ml), frozen, and freeze-dried. Such dried sheets, coated with a thin sponge-like layer of Zyderm collagen were then activated with an ethanol solution of COH102 and COH206 (each component at 10% w/v concentration). These were referred to as "acidic KN sheets". An alternative procedure utilized dried Semed F sheets (dried from acidic slurry), coated once with Zyderm collagen sheets, and incubated for 3 hours in water adjusted to pH 9-10. Additional sodium hydroxide was added as necessary to keep the solution plus sheets at pH 9-10. The sheets were recovered from the solution and dried overnight at 37° C. The sheets were then re-coated with Zyderm collagen at 12 mg/ml, frozen, freeze-dried, and finally impregnated with active PEG in ethanol to yield the dried, active samples, termed "basic KN sheets".

A shear failure test for active sheets was developed using the devices depicted in FIG. 6. Coarse fibered collagen sheets either activated with PEG or as normally prepared for the burst test, were cut to 1×3 cm sizes (termed "strips"). Plastic tabs or adhesive tape was secured over one end, covering a 1 cm square area of the strip. The plastic tabs were secured to the hide grindate strip with cyanoacrylate glue. A hole approximately 2 mm in diameter was pierced in the plastic tab or in the tape. Over a 1 cm square area of a collagen sheet was placed approximately 300 μl of pH 9.6 PC buffer. An active PEG/collagen sheet was then placed on the buffer wetted hide grindate and held with light pressure for 30 sec. In this way the bonded surface was 1 cm square. Hooks were then placed through the holes at the end of each strip, and the bonded strips were suspended to a suitable support. To the lower hook were added metal washers (average weight per washer: 1.63 g) to incrementally increase the shearing force on the bonded surface. The weight required to pull the bonded surface apart was recorded. Variations in the nature of the bonding surfaces and bonding formulations were studied, including using control strips containing collagen sponge on the surface but no active PEG and also bonding of hide grindate strips with cyanoacrylate.

One set of samples involved the bonding of one untreated hide grindate strip to a collagen sponge-coated strip (containing no active PEG). Another set of samples were performed with the same pairs of strips, but this time a COH102/COH206 mixture was added to the apposed strips and allowed to gel. The gelling mixture was as follows:

10 mg COH102 plus 40 μl pH 6.0 0.5 mM phosphate buffer
10 mg COH206 plus 40 μl pH 8.9 300 mM phosphate buffer Such a mixture gels in about 15 seconds, which allows ample time to add the gel mixture to one strip, press the second strip on top, and wait 30 sec for gelation to occur.

For bonding of strips with cyanoacrylate, the test strip was first moistened with PC buffer (200 μl for a 1 cm square area). Then a second strip coated with cyanoacrylate was pressed on top of the first. As with active PEG sheets, only moderate pressure was used to maintain apposition during the 30 sec bonding time.

Results:

Acidic KN sheets and basic KN sheets were subjected to burst testing; 1 cm square pieces were placed over the test hide grindate sheet already wetted with PC buffer. Acidic KN sheets exhibited very low burst strengths (2 and 4 mm Hg). Basic KN sheets gave values similar to previous results with coated collagen sheets (324, 286, and 311 mm Hg).

The shear failure method was used to compare bonding of collagen sheets under several conditions (Table 15). For sheets bonded by COH102/COH206, very poor bond strengths were observed. Active PEG sheets exhibited bond strengths similar to that observed with cyanoacrylate.

TABLE 15

Shear Failure of Bonds for Various Sheet Materials

| Material | Bond Rupture Force (g) |
|---|---|
| Sheet + Sponge (control) | 55.4, 53.8 |
| Sheet + COH 102/COH206 | 14.7, 13.0 |
| Sheet + Cyanoacrylate | 272 |
| Sheet + Active PEG | >217, >466* |

*Ultimate bond strengths not determined; in both cases the collagen sheet tore, or the fixation of hooks failed, not the bonded area.

We claim:

1. A biocompatible polymer device comprising a collagen sponge or sheet impregnated with a two-part reactive polyethylene glycol powder, wherein said reactive powder comprises a first polyethylene glycol having m nucleophilic groups and a second polyethylene glycol having n electrophilic groups, wherein the polyethylene glycol powder remains unreactive in the dry state, wherein said first polyethylene glycol is a tetra-functional thiol polyethylene glycol and said second polyethylene glycol is a tetra-functional glutaryl-succinimidyl polyethylene glycol.

2. The biocompatible polymer device according to claim 1, wherein the first polyethylene glycol having m nucleophilic groups is penta-erythritol polyethylene glycol ether tetrathiol with a molecular weight of about 10,000 and the second polyethylene glycol having n electrophilic groups is penta-erythritol polyethylene glycol ether tetra succinimidyl-glutarate with a molecular weight of about 10,000.

3. A biocompatible polymer device according to claim 1 further comprising a tensile strength enhancer comprised of a material selected from the group consisting of polyglycolide, polylactide, polyglycolide-polylactide copolymers, glass wool, plastics, resins, and combinations thereof.

4. A biocompatible polymer device according to claim 1 further comprising an additional compound selected from the group consisting of glycosaminoglycans, proteins, and peptide fragments.

5. A biocompatible polymer device according to claim 3, wherein the additional compound is a protein selected from the group consisting of collagen, fibronectin, gelatin, albumin, or peptide fragments thereof.

* * * * *